(12) United States Patent
Koh et al.

(10) Patent No.: US 12,024,562 B2
(45) Date of Patent: Jul. 2, 2024

(54) ANTIBODY BINDING TO TIE2 AND USE THEREOF

(71) Applicant: INSTITUTE FOR BASIC SCIENCE, Daejeon (KR)

(72) Inventors: Gou Young Koh, Daejeon (KR); Jeomil Bae, Daejeon (KR); Jaeryung Kim, Daejeon (KR)

(73) Assignee: Institute for Basic Science, Daejeon (KR)

( * ) Notice: Subject to any disclaimer, the term of this patent is extended or adjusted under 35 U.S.C. 154(b) by 570 days.

(21) Appl. No.: 17/111,413

(22) Filed: Dec. 3, 2020

(65) Prior Publication Data

US 2021/0179719 A1 Jun. 17, 2021

Related U.S. Application Data

(63) Continuation of application No. PCT/KR2019/006820, filed on Jun. 5, 2019.

(60) Provisional application No. 62/682,042, filed on Jun. 7, 2018.

(30) Foreign Application Priority Data

Jun. 5, 2019 (KR) .................. 10-2019-0066622

(51) Int. Cl.
| | |
|---|---|
| *C07K 16/28* | (2006.01) |
| *A61K 31/713* | (2006.01) |
| *A61K 39/395* | (2006.01) |
| *A61K 45/06* | (2006.01) |
| *A61P 27/06* | (2006.01) |
| *C12N 5/10* | (2006.01) |
| *C12N 15/63* | (2006.01) |
| *A61K 39/00* | (2006.01) |

(52) U.S. Cl.
CPC ........ *C07K 16/2863* (2013.01); *A61K 31/713* (2013.01); *A61K 39/3955* (2013.01); *A61K 45/06* (2013.01); *A61P 27/06* (2018.01); *C12N 5/10* (2013.01); *C12N 15/63* (2013.01); *A61K 2039/505* (2013.01); *C07K 2317/24* (2013.01); *C07K 2317/34* (2013.01); *C07K 2317/565* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 6,365,154 B1 | 4/2002 | Holmes et al. |
| 7,658,924 B2 | 2/2010 | Oliner et al. |
| 8,987,420 B2 | 3/2015 | Thurston et al. |
| 9,017,670 B2 | 4/2015 | Thurston |
| 9,505,841 B2 | 11/2016 | Kim et al. |
| 9,683,051 B2 | 6/2017 | Kamohara et al. |
| 2004/0101920 A1 | 5/2004 | Radziejewski et al. |
| 2009/0137416 A1 | 5/2009 | Fandl et al. |
| 2013/0209492 A1* | 8/2013 | Thurston ............... C07K 16/40 530/387.9 |
| 2017/0174789 A1 | 6/2017 | Thurston |

FOREIGN PATENT DOCUMENTS

| | | |
|---|---|---|
| AU | 1995018745 | 8/1995 |
| CN | 106994185 A | 8/2017 |
| JP | 2000041675 A | 2/2000 |
| JP | 2011102273 A | 5/2011 |
| JP | 2015168656 A | 9/2015 |
| JP | 2018043949 A | 3/2018 |
| KR | 1020140054303 A | 5/2014 |
| KR | 1020150032075 A | 3/2015 |
| KR | 1020170029508 A | 3/2017 |
| WO | 0018437 A1 | 4/2000 |
| WO | 2013028442 A1 | 2/2013 |

OTHER PUBLICATIONS

Edwards et al., J. Mol. Biol. (2003) 334, 103-118.*
Hansbury et al., "Production and characterization of a Tie2 agonist monoclonal antibody," Angiogenesis, 2001, 4(1):29-36.
Hwang et al., "Stimulation of angiogenesis and survival of endothelial cells by human monoclonal Tie2 receptor antibody," Biomaterials, 2015, 15:119-128.
Partial European Search Report received in European Application No. 19814472.7, dated Mar. 2, 2022, 18 pages.
Teichert-Kuliszewska et al., "Biological action of angiopoietin-2 in a fibrin matrix model of angiogenesis is associated with activation of Tie2," Cardiovascular Research, 2001, 49(3):659-670.
Cho et al., "COMP-Ang1: A designed angiopoietin-1 variant with nonleaky angiogenic activity," PNAS, 2004, vol. 101, No. 15, pp. 5547-5552.
David S et al., "Effects of a synthetic PEG-ylated Tie-2 agonist peptide on endotoxemic lung injury and mortality," 2011, Am J Physiol Lung Cell Mol Physiol, 300: L851-L862.
Frye M, "Interfering with VE-PTP stabilizes endothelial junctions in vivo via Tie-2 in the absence of VE-cadherin," J. Exp. Med. 2015 vol. 212 No. 13 2267-2287.
GenBank: XP 016816188.1. angiopoietin-1 receptor isoformX3 [Pan troglodytes]. (Mar. 20, 2018).
Goel S et al., "Effects of Vascular-Endothelial Protein Tyrosine Phosphatase Inhibition on Breast Cancer Vasculature and Metastatic Progression," 2013, J Natl Cancer Inst, vol. 105, Issue 16, 1188-1201.

(Continued)

*Primary Examiner* — Marianne P Allen
(74) *Attorney, Agent, or Firm* — McNeill Baur PLLC

(57) ABSTRACT

The present invention refers to an antibody against Tie-2 or antigen-binding fragment thereof, a nucleic acid encoding the same, a vector comprising the nucleic acid, a cell transformed with the vector, a manufacturing method of the antibody or antigen-binding fragment thereof, and a composition for preventing or treating angiogenic diseases, which comprises the antibody or antigen-binding fragment thereof.

6 Claims, 8 Drawing Sheets

Specification includes a Sequence Listing.

(56) References Cited

OTHER PUBLICATIONS

Hayashi M, et al., "VE-PTP regulates VEGFR2 activity in stalk cells to establish endothelial cell polarity and lumen formation," 2013, Nature Communication, 1-15.

International Search Report corresponding to International Patent Application No. PCT/KR2019/006820, dated Sep. 16, 2019, 3 pages.

Marth C et al., "ENGOT-ov-6/Trinova-2: Randomised, double-blind, phase 3 study of pegylated liposomal doxorubicin plus trebananib or placebo in women with recurrent partially platinum-sensitive or resistant ovarian cancer," 2017, Eur. J. Cancer, 70:111-121.

Mellberg S et al., "Transcriptional profiling reveals a critical role for tyrosine phosphatase VE-PTP in regulation of VEGFR2 activity and endothelial cell morphogenesis," 2009, Faseb J., vol. 23, 1490-1502.

Moore J. O. et al., "Dimerization of Tie2 mediated by its membrane-proximal FNIII domains," PNAS, Apr. 25, 2017, vol. 114, No. 17, pp. 4382-4387.

Saharinen P et al., "Therapeutic targeting of the angiopoietin-TIE pathway," 2017, Nature Review Drug Discovery, vol. 16, 636-661.

Machine translation of CN106994185, Aug. 1, 2017, He et al., 18 pages.

\* cited by examiner

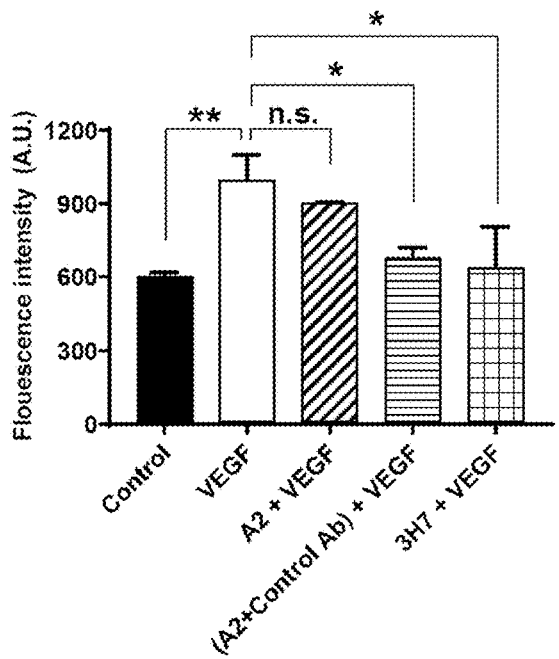
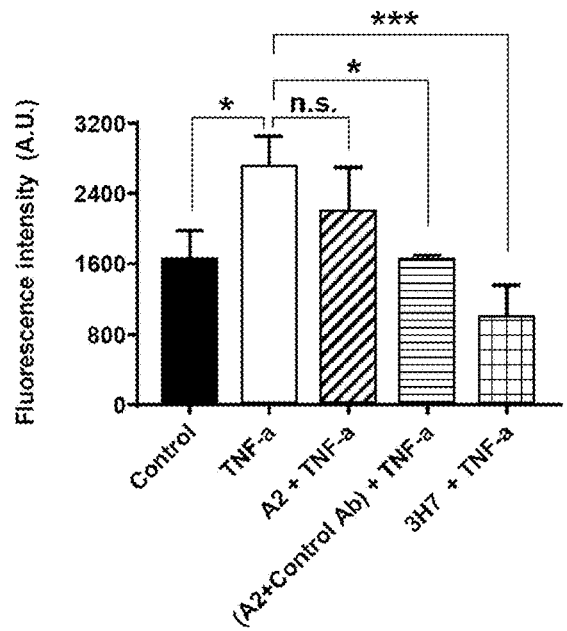
*Fig. 4A*    *Fig. 4B*
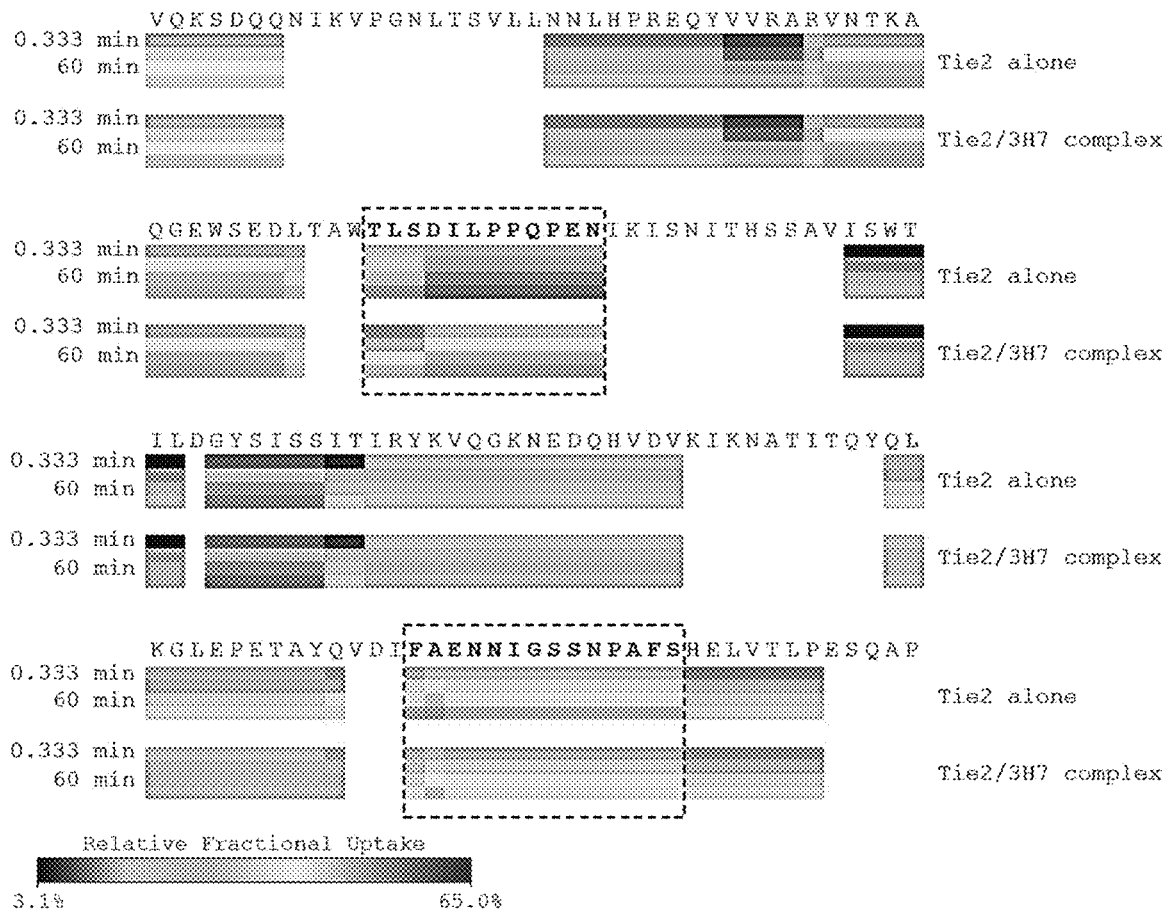
*Fig. 5*

Crystal structure of Human Tie2 FNIII (PDB: 5UTK)

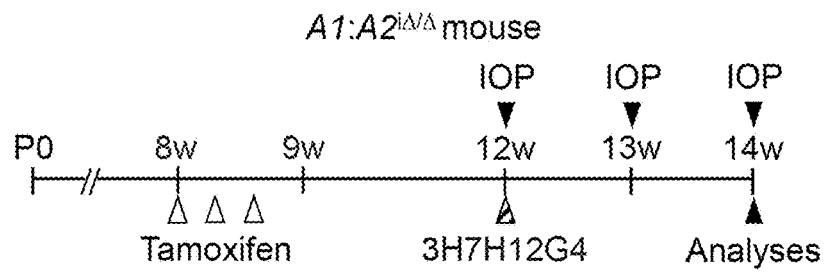
*Fig. 8A*
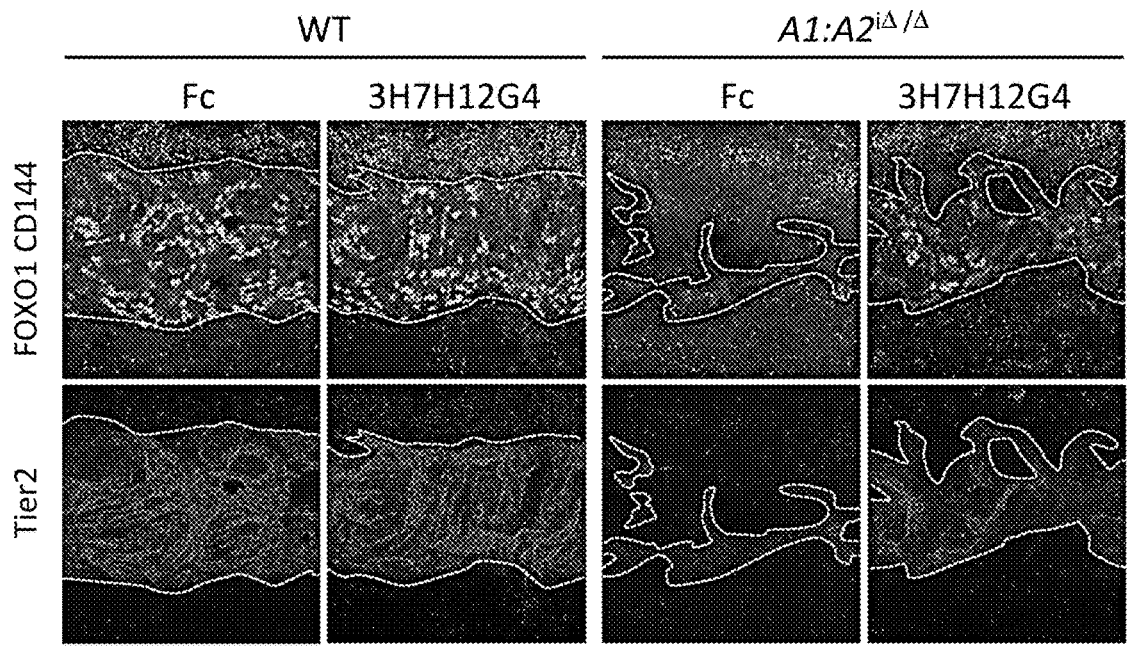
*Fig. 8B*
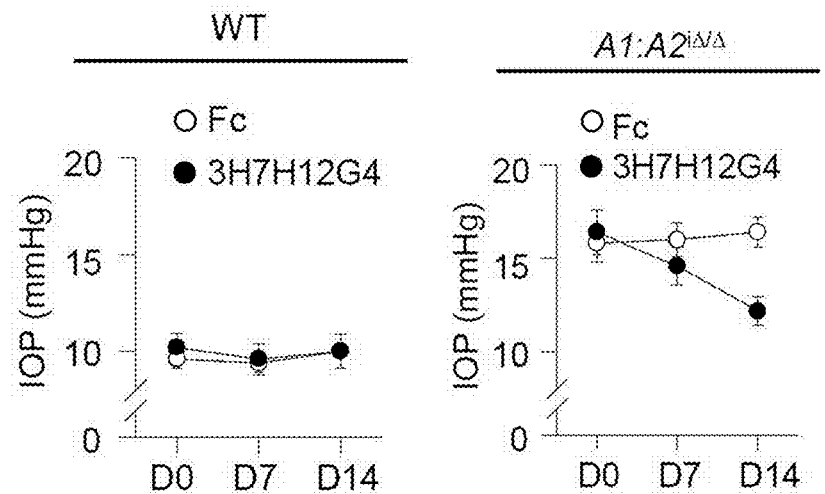
*Fig. 8C*    *Fig. 8D*

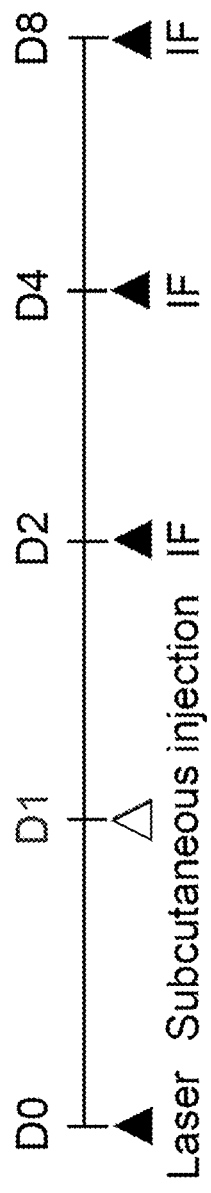
*Fig. 10A*
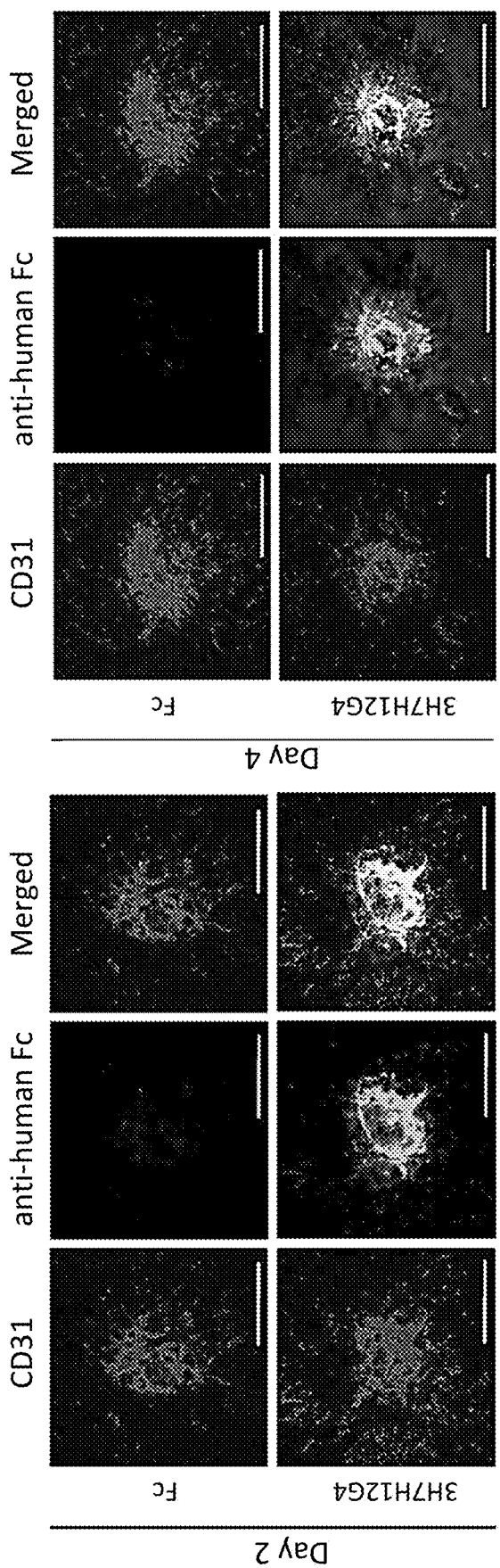
*Fig. 10B*
*Fig. 10C*

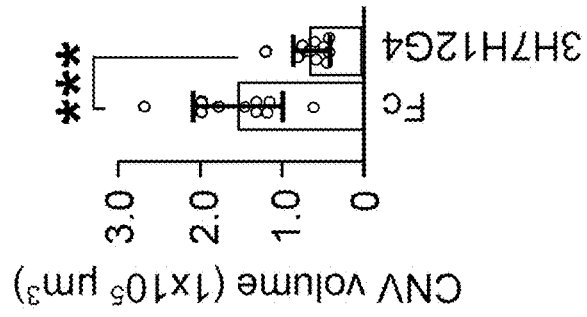
Fig. 11A
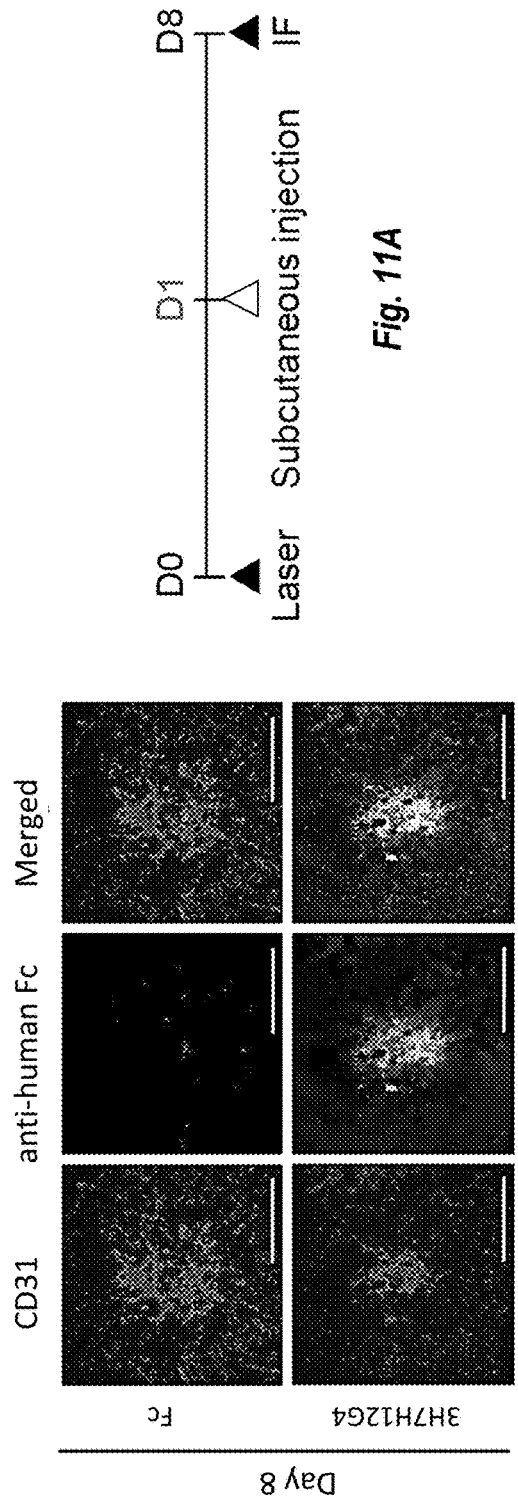
Fig. 10D
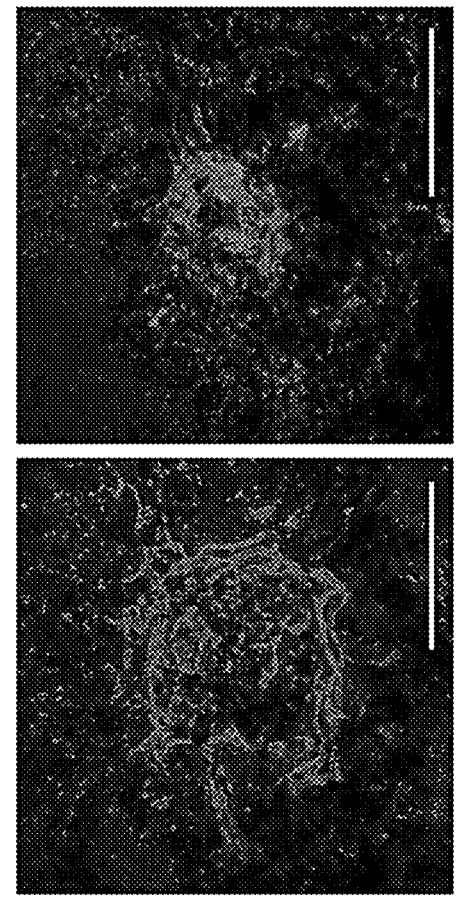
Fig. 11B
Fig. 11C

ANTIBODY BINDING TO TIE2 AND USE THEREOF

This application is a continuation of International Patent Application No. PCT/KR2019/006820, filed Jun. 5, 2019, which claims the benefit of Korean Patent Application No. 10-2019-0066622, filed Jun. 5, 2019, and U.S. Provisional Patent Application No. 62/682,042, filed Jun. 7, 2018, all of which are incorporated herein by reference in their entirety for all purposes.

This application contains a Sequence Listing in computer readable form entitled "2020-11-04_01262-0003-00US_Seq_List_ST25.txt," created Nov. 4, 2020, having a size of 49,005 bytes, which is incorporated by reference herein.

FIELD OF THE INVENTION

The present invention relates to an antibody against Tie-2 or an antigen-binding fragment thereof, a nucleic acid encoding the same, a vector containing the nucleic acid, a cell transformed with the vector, a method for preparing the antibody or antigen-binding fragment thereof, and a pharmaceutical composition to prevent or treat angiogenic diseases.

DESCRIPTION OF THE BACKGROUND

Angiogenesis occurs dynamically by a variety of regulatory factors during the development, growth, maintenance, and homeostasis of an organism. Blood vessels newly formed in this process act as transport channels for various biomaterials such as nutrients, oxygen, and hormones in the surrounding cells. Functionally and structurally abnormal blood vessels are the direct or indirect cause for the initiation and progression of various diseases. Tumor blood vessels aggravate hypoxia due to their defective function and structure, resulting in tumor progression and metastasis to other tissues, and also in the poor delivery of anticancer drugs into the core of the tumor mass. Defective blood vessels are also found in other various diseases and conditions, in addition to cancer. Examples thereof include various ocular diseases (e.g., diabetic macular edema, wet age-related macular degeneration), viral infections, and acute inflammatory responses such as sepsis. Thus, if a therapeutic agent capable of normalizing pathologic blood vessels is available, it can be applied to the treatment of various patients with vascular abnormalities.

The angiopoietin family plays an important role in the formation and maintenance of blood vessels, and is comprised of four angiopoietins (Ang1, Ang2, Ang3, and Ang4). Angiopoietin-1 (Ang1) binds to the Tie2 receptor present on the surface of vascular endothelial cells to phosphorylate and activate Tie2 receptor, resulting in stabilization of blood vessels. On the other hand, angiopoietin-2 (Ang2) binds to the Tie2 receptor, but acts as an antagonist to induce inactivation of the Tie2 receptor, resulting in destabilization of blood vessels and leakage of blood vessels. It was reported that the expression level of Ang2 is highly increased in the blood of cancer patients, ocular diseases, viral and bacterial infections and inflammatory diseases (Saharinen P et al., 2017, Nature Review Drug Discovery). However, Ang2 is also known to act as an agonist to induce activation of the Tie2 receptor in several processes, including lymphatic tube formation and maintenance, and thus it is believed that Ang2 performs various functions depending on the context.

Up to now, development and clinical test of various Anti-Ang2 antibodies have been intensively focused by many biopharmaceutical companies (e.g., U.S. Pat. Nos. 7,658,924, and 8,987,420). These Ang2 antibodies are shown to inhibit the binding of Ang2 to Tie2 and these Ang2 neutralizing effect was eventually shown to hinder the formation of new blood vessel. The anti-angiogenic and anti-cancer activities of these anti Ang2-antibodies have been demonstrated in many preclinical models, and diverse anti-Ang2 antibodies are being clinically tested in various cancer patients. However, their anti-cancer efficacy has been demonstrated to be insufficient. For example, Phase 3 clinical trials conducted by Amgen showed that the anti-cancer efficacy of the Ang2 antibody in ovarian cancer patients was insignificant (Marth C et al., 2017, Eur. J. Cancer). In addition to cancer models, a Ang2 neutralizing antibody, Nesvacumab, was tested in ocular patients, however it failed to improve the efficacy of Eylea (anti-VEGF) in the clinical phase 2 combo-study.

In contrast to the above-mentioned Ang2 neutralization approach, direct Tie2 activation has been also considered as an alternative approach to inhibit angiogenesis and suppress vascular permeability. Recombinant proteins, which bind directly to the Tie2 receptor and induce phosphorylation and activation of Tie2, have also been developed and tested in many preclinical cancer and ocular models. Examples thereof include COMP-Ang1 (Cho et al., 2004, PNAS) and Vasculotide (David S et al., 2011, Am J Physiol Lung Cell Mol Physiol). Although these agents showed anti-angiogenic and anti-permeability activity, these have very short half-life and unstable physicochemical properties. In addition, a small molecule compound (AKB-9778) was developed as an inhibitor for a phosphatase, VE-PTP which inactivate Tie2 by removing a phosphate group from phosphorylated Tie2 (Goel S, 2013, J Natl Cancer Inst). This compound indirectly increases Tie2 activity by inhibiting VE-PTP, although it has the disadvantage of activating other receptors as well (Frye M, 2015, J Exp. Med, Hayashi M, 2013, Nature Communication, Mellberg S et al., 2009, FASEB J.). In addition, agonistic Tie2 antibodies have been developed (U.S. Pat. No. 6,365,154B1, US20170174789A1). These antibodies increased the survival of endothelial cells and inhibited the vascular leakage. Interestingly, herbal extracts were shown to activate Tie2 activity and claimed to be used as skin care cosmetics (for example, JP2011102273A, JP2018043949A, JP2015168656A).

Under this technical background, the inventors of the present application made an effort to develop antibodies which specifically bind to Tie2. As a result, the inventors developed Tie2 antibodies that bind with affinity, and confirmed that these Tie2 antibodies can play a role as a therapeutic agent for angiogenic disease by inducing the phosphorylation and the activation of the Tie2 receptor, and completed the present invention.

SUMMARY OF THE INVENTION

The object of the present invention is to provide a new anti-Tie2 antibody or antigen-binding fragment thereof.

Another object of the present invention is to provide a nucleic acid encoding the antibody or antigen-binding fragment thereof.

Another object of the present invention is to provide a vector containing the nucleic acid, a cell transformed with the vector and a method for producing the same.

Another object of the present invention is to provide a composition comprising the antibody or antigen-binding fragment thereof for preventing or treating angiogenic diseases.

Another object of the present invention is to provide a composition for comprising the antibody or antigen-binding fragment thereof and for co-administration with other therapeutic agents for angiogenic diseases.

In order to achieve the above object, the present invention provides anti-Tie2 antibody or antigen-binding fragment thereof that binds to the Ig3-FNIII (1-3) domain comprising the sequence of SEQ ID NO: 2.

Specifically, the present invention provides also anti-Tie2 antibody or antigen-binding fragment thereof comprising a heavy chain variable region comprising heavy chain CDRs comprising the amino acid sequences of SEQ ID: 3 to 5, a light chain variable region comprising light chain CDRs comprising the amino acid sequences of SEQ ID: 6 to 8; a heavy chain variable region comprising heavy chain CDRs comprising the amino acid sequences of SEQ ID: 13 to 15, a light chain variable region comprising light chain CDRs comprising the amino acid sequences of SEQ ID: 16 to 18; a heavy chain variable region comprising heavy chain CDRs comprising the amino acid sequences of SEQ 23 to 25, a light chain variable region comprising light chain CDRs comprising the amino acid sequences of SEQ ID: 26 to 28; a heavy chain variable region comprising heavy chain CDRs comprising the amino acid sequences of SEQ ID: 33 to 35, a light chain variable region comprising light chain CDRs comprising the amino acid sequences of SEQ ID: 36 to 38; or a heavy chain variable region comprising heavy chain CDRs comprising the amino acid sequences of SEQ ID: 43 to 45, a light chain variable region comprising light chain CDRs comprising the amino acid sequences of SEQ ID: 46 to 48.

The present invention provides also a nucleic acid encoding the antibody or antigen-binding fragment thereof.

The present invention provides also a vector encoding the nucleic acid.

The present invention provides also a cell transformed with the vector.

The present invention also provides a manufacturing method of the antibody or antigen-binding fragment thereof including the next steps: (a) the step for culturing the cell thereof; and (b) the recovering step for the antibody or antigen-binding fragment thereof from the cell.

The present invention also provides a composition for preventing or treating angiogenesis-related diseases including the antibody or antigen-binding fragment thereof as an active ingredient.

The present invention also provides a composition for co-administration with other angiogenic disease therapeutic agent including the antibody or antigen-binding fragment thereof.

BRIEF DESCRIPTION OF THE DRAWINGS

FIGS. 4A-4B show inhibition of VEGF or TNF-a induced-vascular permeability by 3H7. HUVECs were seeded on transwell chamber and grown for 3 days. At 100% confluence, HUVECs were pre-treated with Ang2 (A2, 1 ug/ml), Ang2 together with Control Ab (A2+Control Ab, 1 ug/ml), or 3H7 (1 ug/ml) for 30 min and treated with VEGF (500 ng/ml) for 45 min (A) or TNF-a (100 ng/ml) for 22 hr (B) into the upper chamber. Vascular permeability was assessed by measuring FITC fluorescence in the lower chamber after adding FITC-dextran for 20 min into the upper chamber. Values are mean±SD. *$p<0.05$, $p<0.01$, * $p<0.001$ by one-way ANOVA.

FIG. 5 shows heat map representing the significant difference region in deuterium uptake when Tie2 alone or Tie2/3H7 complex was tested in hydrogen/deuterium (H/D) exchange-mass spectrometry analysis. Heat map of deuterium uptake per residue at 0.333, 10, 60, and 240 min for hTie2 antigen was generated in the absence or presence of anti-Tie2 antibody 3H7 using the data of H/D exchange-mass spectrometry. The heat map analysis of the deuterium uptake difference indicated that the epitopes to which antibody 3H7 binds are residues 633 to 644 (SEQ ID NO: 1, TLSDILPPQPEN) and 713-726 (SEQ ID NO: 1, FAENNIGSSNPAFS) of hTie2 (Table 13). The complete sequence shown in FIG. 5 is residues 583-738 of SEQ ID NO: 1. Grey scale indicates the percentage of H/D exchange per residue between the Tie2 alone and Tie2/3H7 mixtures at each individual time.

FIGS. 8A-8F show increased area of SC and decreased IOP by humanized Tie2 antibody 3H7H12G4 in a mouse model of primary open-angle glaucoma. Tamoxifen administration for inducible deletion of both angiopoietin-1 and -2 was performed at 8-weeks-old A1:A2$^{i\Delta/\Delta}$ mice. The intraocular administration of 3H7H12G4 (one eye, 1 μl injection of 5 mg/ml solution) and Fc (contralateral eye, 1 μl injection of 5 mg/ml solution) was performed at 12 weeks old. Periodic measurement of intraocular pressure (IOP) was performed at 12, 13 and 14 weeks old. CD144$^+$ SC area and intensities of Prox1 and Tie2 immunostaining in CD144$^+$ SC were measured at 2 weeks after 3H7H12G4 administration. Scale bar, 100 µm. n=5 for each group. Values are mean±SD. *p<0.05 by Kruskal-Wallis test followed by Tukey's HSD test with ranks.

FIGS. 10A-10D is the result about co-localization of 3H7H12G4 and CD31 in endothelial cells of CNV area. The subcutaneous administration of 3H7H12G4 was performed at 1 day after laser photocoagulation. The co-localization of 3H7H12G4 and CD31 in endothelial cells of CNV was directly detected by anti-human IgG secondary antibody at 2, 4, and 8 days after laser photocoagulation.

FIGS. 11A-11C is the result about suppression by subcutaneously injected 3H7H12G4. The subcutaneous administration of 3H7H12G4 was performed at 1 day after laser photocoagulation. CD31$^+$ CNV volumes were measured at 8 days after laser photocoagulation. Scale bar, 100 µm. n=10 for each group. Values are mean±SD. ***p<0.001 by unpaired Student's t-test.

DETAILED DESCRIPTION AND PREFERRED EMBODIMENTS OF THE INVENTION

Figure 1:
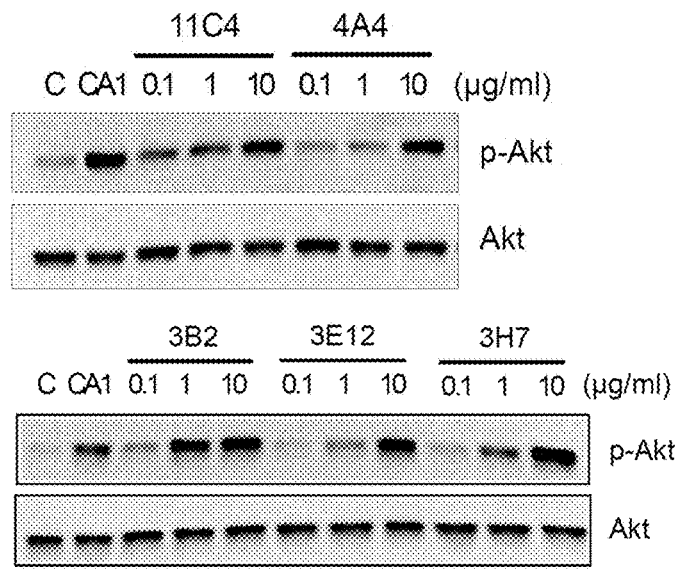
FIG. 1 shows analysis of Akt phosphorylation induced by anti-Tie2 antibodies. HUVECs were serum-starved for 6 hr and incubated with COMP-Ang1 (CA1, 0.5 μg/ml) or anti-Tie2 antibodies (11C4, 4A4, 3B2, 3E12 and 3H7) for 30 min. Cell lysates were subjected to SDS-PAGE/Western blotting and blots were probed with anti-phospho-Akt (S473) or anti-Akt antibody.

Unless defined otherwise, all technical and scientific terms used herein have the same meaning as those appreciated by those skilled in the field to which the present disclosure pertains.

The inventors of the present application confirmed Tie2 antibody as an increasing agent of Tie2 activity by binding to the Tie2 Ig3-FNIII (1-3) domain containing the sequence of SEQ ID NO:2.

Tie2 is a receptor protein that promotes the differentiation and stabilization of blood vessels, highly expressed in blood vessels, and if activated, the Tie2 receptor stabilizes cancer blood vessels and it becomes possible to gather surrounding support cells. By the antibodies or antigen-binding fragment thereof according to the invention, activated Tie2 in cancer vessels normalizes cancer vessels, eliminating the increased hypoxia within the tumor, supplying the sufficient oxygen by increasing blood flow into the tumor, and increasing the delivery of other anticancer drugs and the penetration of immune cells.

In this respect, the present invention relates to a Tie2 antibody or antigen-binding fragment thereof that binds to the Tie2 Ig3-FNIII (1-3) domain comprising the sequence of SEQ ID NO: 2.

As used herein, the term "antibody" means an antibody specifically binding to Tie2. In the scope of the present invention, in addition to a complete antibody specifically binding to Tie2, antigen-binding fragments of the antibody molecule are also included.

A complete antibody has the structure of two full-length light chains and two full-length heavy chains, and each light chain is connected to a heavy chain by a disulfide bond. The constant region of the heavy chain has gamma (γ), mu (µ), alpha (α), delta (δ) and epsilon (ε) types, with the subclasses of Gamma 1 (γ1), Gamma 2 (γ2), Gamma 3 (γ3), Gamma 4 (γ4), Alpha 1 (α1) and alpha 2 (α2). The constant region of the light chain has kappa (κ) and lambda (λ) types.

Antigen-binding fragments or antibody fragments of an antibody means a fragment which can bind to an antigen, and includes Fab, F(ab'), F(ab')2 and Fv. Among antibody fragments, Fab has one antigen-binding site with a structure of the variable regions of the light and heavy chain, the constant region of the light chain, and the first CH1 of the heavy chain.

Fab' differs from Fab in that it has a hinge region comprising one or more cysteine residues at the C-terminus of the CH1 domain. F(ab')2 antibody is produced by disulfide bonds formation between Cysteine residues in the region of the hinge of Fab'. Fv is the smallest antibody fragment having only the variable region of the heavy chain and the variable region of the light chain. Double chain Fv (two-chain Fv) is formed by a non-covalent bond between the heavy chain variable region and the light chain variable region, and single-chain Fv (scFv) is generally formed through a peptide linker covalently between the variable region of the heavy chain and the variable region of the light chain, or is connected directly at the C-terminus by forming a dimer-like structure like a double-chain Fv. This fragment can be obtained by protein hydrolysis enzyme (e.g., you can get Fab by restriction digestion of whole antibody using papain, you can get F(ab')2 fragment by cutting with pepsin), also made by genetic manipulation technology.

In one embodiment, the antibody according to the invention is the Fv form (e.g., scFv), or a complete antibody form. In addition, constant region of the heavy chain may be selected from any isotypes of gamma (γ), mu (µ), alpha (α), delta (δ), or epsilon (ε). For example, the constant region is gamma 1 (IgG1), gamma 3 (IgG3), or gamma 4 (IgG4). The light chain constant region can be of kappa or lambda type.

The term in the present invention, "heavy chain", means the full-length heavy chain or fragments thereof comprising a variable region domain VH and three constant region domains CH1, CH2 and CH3, having an amino acid sequence with a sufficient variable region in order to provide antigen specificity. In addition, the term in the present invention, "light chain", means the full-length light chain or fragments thereof comprising a variable region domain VL and a constant region domain CL, having an amino acid sequence with a sufficient variable region in order to provide antigen specificity.

The antibodies of the present invention are monoclonal antibodies, multispecific antibodies, human antibodies, humanized antibodies, chimeric antibodies, single chain Fvs (scFV), single chain antibodies, Fab fragments, F(ab') fragments, Disulfide-binding Fvs (sdFV) and anti-idiotype (anti-Id) antibodies, or of the above antibodies epitope-binding fragments and the like are included, but are not limited thereto.

The monoclonal antibody is an antibody obtained from a population of substantially homogeneous antibodies, i.e. refers to the same individual antibodies in the population which may be present in trace amounts except for the possible natural mutation. Monoclonal antibody is highly specific, and it is induced against a single antigenic site. In contrast to the conventional (polyclonal) antibody which typically includes different antibodies instructed by different epitopes, each monoclonal antibody is instructed by a single determining factor.

"Epitope" means a protein determinant to which an antibody can specifically bind to. Epitopes are usually a group of chemically active surface molecules, e.g. it is composed of amino acids or sugar side chains, and generally has a specific charge characteristic as well as a specific three-dimensional structural characteristic. Stereoscopic epitope and non-stereoscopic epitope lose its bonds to the former in the presence of a denaturing solvent, but it does not lose bonds to the latter.

The Tie2 antibody or antigen-binding fragment thereof according to the present invention, when the epitope is identified through hydrogen/deuterium exchange, binds to 633 to 644 amino acids of Tie2 comprising the sequence of SEQ ID NO: 1 TLSDILPPQPEN and/or at amino acids 713 to 726 FAENNIGSSNPAFS.

The "humanized" form of non-human (e.g. murine) antibody is a chimeric antibody comprising one or more amino acid sequence (e.g. CDR sequence) from one or more non-human antibodies (donor or source antibodies) having a minimal sequence derived from non-human immunoglobulins. In most cases, the humanized antibody is a human immunoglobulin (recipient antibody) whose residues of hypervariable region are replaced by residues from hypervariable regions of non-human species (donor antibody), for example, mouse, rat, rabbit or non-human primate, possessing the desired specificity, affinity and ability. For humanization, one or more residues in the framework domain (FR) of the variable regions of the recipient human antibody can be replaced by the corresponding residues from a non-human species donor antibody. Through this, it helps to maintain a proper three-dimensional configuration of the grafted CDR(s), thereby improving affinity and antibody stability. Humanized antibodies can include a new additional residue that does not appear in the recipient antibody or donor antibody, e.g., to further refine the performance of antibody.

The "humanized antibody" as a molecule derived from human immunoglobulin means that the entire amino acid sequence constituting the antibody, including the complementary determining region and structural region, is composed of human immunoglobulin.

Any "chimeric" antibodies (immunoglobulins) as well as the fragment of the above-mentioned antibody, which exhibit the desired biological activity, are included where part of the heavy and/or light chain derived from a particular species, or identical or homologous to the corresponding sequence in the antibody belonging to the subclass, while the remaining chain(s) are derived from another species, or belonging to other antibody classes or identical to the corresponding sequence in the antibody belonging to the subclass.

According to a specific example of the present application, 11C4, 4A4, 3B2, 3E12 and 3H7 antibodies which are mouse-derived Tie2 antibodies were produced, and 3H7H11G4, 31-17H1204, 3H7H21G4 or 3H7H22G4 antibodies which were CDR-grafted and humanized from the mouse-derived 31-17 antibody as a source antibody were produced.

"Antibody variable domain" as used herein refers to light and heavy chain parts of an antibody molecule comprising the amino acid sequences of complementarity determining regions (CDR; i.e., CDR1, CDR2, and CDR3) and framework regions (FR). VII refers to the variable domain of the heavy chain. VL refers to the variable domain of the light chain.

"Complementarity determining regions" (CDRs; i.e., CDR1, CDR2, and CDR3) refers to the amino acid residues of the variable domain of the antibody, which are necessary for antigen binding. Each variable domain typically, has three CDR regions identified as CDR1, CDR2 and CDR3.

In one embodiment, the Tie2 antibody or antigen-binding fragment thereof may include a heavy chain variable region comprising heavy chain CDRs, comprising the amino acid sequences of SEQ ID NOs:3-5, a light chain variable region comprising light chain CDRs comprising the amino acid sequences of SEQ ID NOs: 6 to 8;

a heavy chain variable region comprising heavy chain CDRs comprising the amino acid sequences of SEQ ID NOs: 13-15, a light chain variable region comprising light chain CDRs comprising the amino acid sequences of SEQ ID NOs: 16 to 18;

a heavy chain variable region comprising heavy chain CDRs comprising the amino acid sequences of SEQ ID NOs:23-25, a light chain variable region comprising light chain CDRs comprising the amino acid sequences of SEQ ID NOs: 26 to 28;

a heavy chain variable region comprising heavy chain CUR having CDRs comprising the amino acid sequences of SEQ NOs:33-35, a light chain variable region comprising light chain CDRs comprising the amino acid sequences of SEQ ID NOs: 36 to 38; or a heavy chain variable region comprising heavy chain CDRs comprising the amino acid sequences of SEQ ID NOs:43-45, a light chain variable region comprising light chain CDRs comprising the amino acid sequences of SEQ ID NOs: 46 to 48.

"Framework region" (FR) is a variable domain residue other than a CDR residue. Each variable domain is typically, has 4 FRs identified as FR1, FR2, FR3 and FR4.

Tie2 antibodies are monovalent or bivalent, and contain single or double chains. Functionally, the binding affinity of the Tie2 antibody is in the range of $10^{-5}$M to $10^{-12}$M.

For example, the binding affinity of the Tie2 antibody is $10^{-6}$ M to $10^{-12}$ M, $10^{-7}$ M to $10^{-12}$ M, $10^{-8}$ M to $10^{-12}$ M, $10^{-9}$ M to $10^{-12}$ M, $10^{-5}$ M to $10^{-11}$ M, $10^{-6}$ M to $10^{-11}$ M, $10^{-7}$ M to $10^{-11}$ M, $10^{-8}$ M to $10^{-11}$ M, $10^{-9}$ M to $10^{-11}$ M, $10^{-10}$ M to $10^{-11}$ M, $10^{-5}$ M to $10^{-10}$ M, $10^{-6}$ M to $10^{-10}$ M, $10^{-7}$ M to $10^{-10}$ M, $10^{-8}$ M to $10^{-10}$ M, $10^{-9}$ M to $10^{-10}$ M, $10^{-5}$ M to $10^{-9}$ M, $10^{-6}$ M to $10^{-9}$ M, $10^{-7}$ M to $10^{-9}$ M, $10^{-8}$ M to $10^{-9}$ M, $10^{-5}$ M to $10^{-8}$ M, $10^{-6}$ M to $10^{-8}$ M, $10^{-7}$ M to $10^{-8}$ M, $10^{-5}$ M to $10^{-7}$ M, $10^{-6}$ M to $10^{-7}$ M or $10^{-5}$ M to $10^{-6}$ M.

The Tie2 antibody or antigen-binding fragment thereof may include a heavy chain variable region comprising the amino acid sequence of SEQ ID NO: 9 and a light chain variable region comprising the amino acid sequence of SEQ ID NO: 11; a heavy chain variable region comprising the amino acid sequence of SEQ ID NO: 19 and a light chain variable region comprising the amino acid sequence of SEQ ID NO: 21; a heavy chain variable region comprising the amino acid sequence of SEQ ID NO: 29 and a light chain variable region comprising the amino acid sequence of SEQ ID NO: 31; a heavy chain variable region comprising the amino acid sequence of SEQ ID NO: 39 and a light chain variable region comprising the amino acid sequence of SEQ ID NO: 41; a heavy chain variable region comprising the amino acid sequence of SEQ ID NO: 49 and a light chain variable region comprising the amino acid sequence of SEQ ID NO: 51; a heavy chain variable region comprising the amino acid sequence of SEQ ID NO: 53 and a light chain variable region comprising the amino acid sequence of SEQ ID NO: 54; a heavy chain variable region comprising the amino acid sequence of SEQ ID NO: 57 and a light chain variable region comprising the amino acid sequence of SEQ ID NO: 58; a heavy chain variable region comprising the amino acid sequence of SEQ ID NO: 61 and a light chain variable region comprising the amino acid sequence of SEQ ID NO: 62; a heavy chain variable region comprising the amino acid sequence of SEQ ID NO: 19 and a light chain variable region comprising the amino acid sequence of SEQ ID NO: 21.

The antibody or antibody fragment of the present invention can include its biological equivalent within a range that can specifically recognize Tie2. For example, it can introduce a change to the amino acid sequence to improve further the binding affinity and/or its other biological properties of the antibody. Such modifications can include, for example, deletion, insertions and/or substitutions of amino acid sequence residues of the antibody. These amino acid variations are made based on the relative similarity of the amino acid substituents, such as hydrophobicity, hydrophilicity, charge, size, etc. of the amino acid side chains. By the analysis of the size, shape and type of amino acid side chain substituents, it is known that arginine, lysine and histidine are all positively charged residues; alanine, glycine and serine have similar sizes; Phenylalanine, tryptophan and tyrosine have a similar shape. Therefore, based on these considerations, we can say that arginine, lysine and histidine, alanine, glycine and serine; and phenylalanine, tryptophan and tyrosine are biologically functional equivalents.

Considering the above-described variation having biologically equivalent activity, it is interpreted that the amino acid sequence of the antibody of the invention or the nucleic acid molecule encoding the same antibody include the sequence in SEQ ID NO and any sequence exhibiting substantial identity. The substantial identity means at least 90% homology, most preferably at least 95% homology, 96% or more, 97% or more, 98% or more, 99% or more sequence homology, when the sequence described in the present invention and any other sequence are aligned as much as possible and analyzed by commonly used algorithm used in the art. The alignment method for sequence comparison is known in the art. NCBI Basic Local Alignment Search Tool (BLAST) is accessible from NBCI, etc., and it can be used in conjunction with a sequence analysis program such as blastp, blasm, blastx, tblastn and tblastx in the internet. BLSAT is accessible at www.ncbi.nlm.nih.gov/BLAST/. The sequence homology comparison method using this program can be found at www.ncbi.nlm.nih.gov/BLAST/blast_help.html.

Based on this, the antibody or antigen-binding fragment thereof of the present invention may have 90%, 91%, 92%, 93%, 94%, 95%, 96%, 97%, 98%, 99%, or more homology, when compared to the specified or all sequence described in the specification. This homology can be determined by sequence comparison and/or alignment by known methods in the art. For example, sequence comparison algorithm (i.e. BLAST or BLAST 2.0), manual alignment, visual inspection can be used to determine the percent sequence homology of a nucleic acid or protein of the present invention.

In another aspect, the present invention relates to nucleic acids encoding the antibody or antigen-binding fragment thereof.

The nucleic acid may comprise the sequence of SEQ ID NO: 10, 12, 20, 22, 30, 32, 40, 42, 50, 52, 55, 56, 59, 60, 63, 64, 67, or 68.

The antibody or the antigen-binding fragment thereof can be produced recombinantly by isolating the nucleic acid encoding the antibody or antigen-binding fragment thereof of the present invention. Further cloning (DNA amplification) by isolating nucleic acids, and inserting it into a replicable vector may be done or further expression may be made. Based on this, the present invention relates to the vector containing the nucleic acid in another aspect.

"Nucleic acid" is meant to encompass DNA (gDNA and cDNA) and RNA molecules inclusively, and nucleotide, the basic structural unit of nucleic acid, includes the nucleotide in nature, as well as the analogue with modified sugar or base moieties. The sequence of the nucleic acid encoding the heavy and light chain variable regions of the present invention can be modified. The modifications include addition, deletion, or non-conservative or conservative substitution of nucleotides.

The DNA encoding the antibody is easily separated or synthesized using a conventional process (for example, by using oligonucleotide probes capable of specifically binding to the DNA encoding the heavy and light chains). Many vectors are available. Vector components generally includes one or more of the following, but is not limited to: signal sequence, origin of replication, one or more marker genes, enhancer element, promoter, and transcription termination sequence.

As used herein, the term "vector", as means for expression a gene of interest in a host cell, includes plasmid vectors, cozmid vector, bacteriophage vector, adenovirus vectors, retroviral vectors and viral vectors such as adeno-associated virus vectors. The nucleic acid encoding the antibody in the vector is operatively linked to a promoter.

"Operatively linked" means the functional linkage between a nucleic acid expression control sequence (for example, promoter, signal sequence, or array of transcriptional regulator binding sites) and different nucleic acid sequences, Thereby, the control sequence controls transcription and/or translation of the other nucleic acid sequence.

In the case of prokaryotic cell as a host, a strong promotor which can process the transcription (for example, tac promoter, lac promoter, lacUV5 promoter, lpp promoter, pLλ promoter, pRλ promoter, rac5 promoter, amp promoter, recA promoter, SP6 Promoter, trp promoter and T7 promoter, etc.), ribosome binding site for initiation of translation and transcription/translation termination sequences are generally included. In addition, for example, in the case of eukaryotic cell as a host, a promoter derived from the genome of mammalian cells (example: metallothionine promoter, β-actin promoter, human hemoglobin promoter and human muscle creatine promoter) or a promotor derived from mammalian viruses (example: adenovirus late promoter, vaccinia virus 7.5K promoter, SV40 promoter, cytomegalovirus (CMV) promoter, tk promoter of HSV, mouse mammary tumor virus (MMTV) promoter, LTR promoter of HIV, Moloney Virus promotor, Epstein Barr Virus (EBV) promoter, and Rous sarcoma virus (RSV) promoter) can be used, and a polyadenylation sequence can be included generally as a transcription termination sequence.

In some cases, the vector may be fused with other sequences to facilitate the purification of the antibody expressed. The sequence to be fused is, for example, glutathione S-transferase (Pharmacia, USA), maltose binding protein (NEB, USA), FLAG (IBI, USA) and 6× His (hexahistidine; Qiagen, USA).

The vector contains an antibiotic resistance gene commonly used in the art as a selection marker, for example a resistant gene to ampicillin, gentamicin, carbenicillin, chloramphenicol, streptomycin, kanamycin, geneticin, neomycin and tetracycline.

In another aspect, the present invention relates to a cell transformed with the above-mentioned vector. Cells used to produce the antibodies of the present invention may be prokaryote, yeast and a higher eukaryotic cell, but not limited thereto.

Prokaryotic host cells such as *Escherichia coli, Bacillus* strains such as *Bacillus subtilis* and *Bacillus thuringiensis, Streptomyces, Pseudomonas* (e.g. *Pseudomonas putida*), *Proteus mirabilis* and *Staphylococcus* (for example, *Staphylococcus carnosus*), can be used.

However, the interest in animal cells is the greatest, the examples of useful host cell lines are COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, or HT1080, but not limited thereto.

In another aspect the present invention relates to, (a) the step for culture of the cell; and (b) the method of manufacturing the antibody and antigen-binding fragment thereof, including recovery step for the antibody or antigen-binding fragment thereof from the cultured cells.

The cells can be cultured in various media. Any commercial culture media can be used without limitation. All other essential supplements known to those skilled in the art may be included in an appropriate concentration. Culture conditions, such as temperature, pH, etc., and selected host cells have already been used, and this will be obvious to those skilled in the art.

Recovery of the antibody or antigen-binding fragment thereof can be made through removing impurities for example using centrifugation or ultrafiltration, and for example using affinity chromatography, etc. Additional extra purification technology such as anion or cation exchange chromatography, hydrophobic interaction chromatography, hydroxyapatite chromatography, and the like can be used.

In another aspect, the present invention relates to the composition containing an active ingredient of the antibody or antigen-binding fragment thereof for preventing or treating angiogenic diseases.

The angiogenesis means the formation or growth of new blood vessels from previously existing blood vessels, "Angiogenesis-related disease" means the occurrence of angiogenesis or a disease associated with progression. If it can be treated with the antibody, the disease may be included in the range of angiogenesis-related diseases without limitation. The examples of the angiogenesis-related diseases are selected from the group composing cancer, metastasis, diabetic retinopathy, retinopathy of prematurity, corneal graft rejection, macular degeneration, neovascular glaucoma, systemic erythrosis, proliferative retinopathy, psoriasis, hemophilic arthritis, capillary formation in atherosclerotic plaques, keloid, wound granulation, vascular adhesion, rheumatoid arthritis, degenerative osteoarthritis, autoimmune diseases, Crohn's disease, restenosis, atherosclerosis, Intestinal adhesions, cat scratch disease, ulcers, liver cirrhosis, nephritis, diabetic nephropathy, diabetes mellitus, inflammatory diseases and neurodegenerative disease, but not limited thereto. In addition, the cancer is selected from the group composing esophageal cancer, stomach cancer, large intestine cancer, rectal cancer, oral cancer, pharynx cancer, larynx cancer, lung cancer, colon cancer, breast cancer, uterine cervical cancer, endometrial cancer, ovarian cancer, prostate cancer, testis cancer, bladder cancer, renal cancer, liver cancer, pancreatic cancer, bone cancer, connective tissue cancer, skin cancer, brain cancer, thyroid cancer, leukemia, Hodgkin's lymphoma, lymphoma, and multiple myeloid blood cancer, but not limited thereto.

The term "prevention" as used herein denotes any action to inhibit or delay the onset of the disease of interest by administering the antibody or composition of the present invention. The term "treatment or therapy" indicates any action that improves or gets better the symptoms of the disease of interest by administering the antibody or composition of the present invention.

The composition comprising the antibody of the present invention is preferably a pharmaceutical composition, and can include a suitable vehicle, excipient or diluent typically used in the field.

Pharmaceutical compositions having a pharmaceutically acceptable vehicle can be various oral or parenteral dosage form such as tablets, pills, powders, granules, capsules, suspensions, oral solutions, emulsions, syrups, sterile aqueous solutions, non-aqueous solutions, suspensions, lyophilizates, and suppository. In relation to the pharmaceutical composition of the present invention can be a diluent or excipient which can be formulated in combination, such as fillers, thickeners, binders, wetting agents, disintegrants, surfactants, etc. Solid preparations for oral administration may be in the form of tablets, pills, powders, granules, capsules, and the like. In connection with the solidarity the compound of the present invention can be formulated by combining one or more excipients such as starch, calcium carbonate, sucrose, lactose, or gelatin. Simple excipient and lubricating agents such as magnesium stearate, talc, and the like may additionally be used.

The liquid preparation for oral administration may be a suspension, an oral solution, an emulsion, a syrup, or the like. Excipients such as water or simple diluents like wet paraffin, a variety of wetting agents, sweeteners, aromatics, preservatives, and etc. can be included in a liquid formulation. In addition, the pharmaceutical compositions in the present invention may be in parenteral dosage form such as sterile aqueous solution, non-aqueous solvent, suspension, emulsion, lyophilisate, suppository, etc. Injectable propylene glycol, polyethylene glycol, vegetable oils such as olive oil and esters such as ethyl oleate may be suitable for insoluble solvent and suspension. The basic substance of the suppository includes Witepsol, macrogol, Tween 61, cacao butter, laurin butter and glycerogelatin.

The composition of the present invention is administered in a pharmaceutically effective amount. Terms used here "A pharmaceutically effective amount" refers to the enough amount of the pharmaceutical composition for disease treatment, with an appropriate benefit/risk ratio which can be applicable for all medical treatments. The effective amount can be different depending on various factors including parameters like the severity of the disease, the patient's age and sex, type of disease, drug activity, drug sensitivity, administration time, route of administration, secretion rate, duration of treatment, co-administration of drugs and other known in the art. The composition in the present invention can be administered by alone or combination with other treatment. In this case, it can be administered sequentially or simultaneously with conventional therapy. Also, the above composition can be administered in single doses or divided into multiple doses. When fully considering these factors, it is important to administer the minimum amount sufficient to obtain maximum effect without side effects and this dosage can be easily determined by an expert. The dosage of the pharmaceutical composition of the present invention is not particularly limited, but it varies depending on various factors, including patient's health status and weight, disease severity, drug type, administration route and administration time.

The composition may be administered into mammals, including rats, mice, livestock, humans, etc., by one time or multiple times a day, via typically accepted routes, for example, orally, rectal, intravenously, subcutaneously, intrauterinely or intracerebrovascularly.

The present invention in other perspective refers to the prevention or treatment methods for angiogenic diseases, and anti-angiogenic methods, including the steps for administering into an individual in need of the antibody or the above composition.

The method of the present invention includes the procedures for administering a pharmaceutical composition of pharmaceutically effective dose for individuals in need of inhibition of angiogenesis. The object is a mammalian such as dog, cow, horse, rabbit, mouse, rat, chicken, and human, but it is not limited thereto. The pharmaceutical composition can be administered via a suitable way including parenterally, subcutaneously, intraperitoneally, intrapulmonarily or intranasally, and if necessary, intralesionally for local treatment. The preferred dosage of the pharmaceutical composition of the present invention is changing depending on various factors including the health status and weight of the individual, the severity of the disease, the type of drug, the route and time of administration, and it can be easily determined by those skilled in the art.

In other aspect the present invention refers to the methods of cancer prevention or treatment, including administering procedures of the composition or the antibody to an individual in need of the antibody and the composition or the pharmaceutical composition for cancer prevention or treatment including the antibody.

Cancer is not limited as long as it is treatable with the antibodies of the present invention. In detail the antibody of the present invention can prevent the occurrence or progression of cancer by inhibiting angiogenesis. Examples of the cancer include esophageal cancer, stomach cancer, large intestine cancer, rectal cancer, oral cancer, pharynx cancer, larynx cancer, lung cancer, colon cancer, breast cancer, uterine cervical cancer, endometrial cancer, ovarian cancer, prostate cancer, testis cancer, bladder cancer, renal cancer, liver cancer, pancreatic cancer, bone cancer, connective tissue cancer, skin cancer, brain cancer, thyroid cancer, leukemia, Hodgkin's lymphoma, lymphoma, and multiple myeloid cancer blood cancer, but is not limited thereto.

In addition, the antibodies of the present invention can be used in combination with other antibodies or biologically active agents or a material for various purposes. The present invention in this respect refers to a composition for combined administration with other therapeutic agents for angiogenic diseases, including the antibody or the antigen-binding fragments thereof.

The other therapeutic agents for angiogenic diseases include anti-angiogenic drugs, anti-inflammatory drugs and/or anticancer drugs. Through this, we can overcome each other's resistance and improve efficacy.

In the composition according to the present invention, when administered in combination with other therapeutic agents for angiogenic diseases, the Tie2 antibody and other therapeutic agents for angiogenic diseases may be administered sequentially or simultaneously. For example, after administering anti-angiogenic drugs, anti-inflammatory drugs and/or anticancer drug into the target individual, the composition having an antibody to Tie2 or an antigen-binding fragment thereof as an active ingredient can be administered, or after the above composition is administered, anti-angiogenic drugs, anti-inflammatory drugs and/or anticancer drug can be administered. Depending on the case, the above composition and the anti-angiogenic drugs, anti-inflammatory drugs and/or anticancer drug can be administered simultaneously to the target individual.

EXAMPLE

Hereafter, the present invention will be described in detail by examples. The following examples are intended merely to illustrate the invention and are not constructed to restrict the invention.

Example 1

Preparation of Mouse Monoclonal Anti-Tie2 Antibody 1.1 Mouse Immunization with Human Tie2

As an immunogen, the Ig3-FNIII (1-3) domains of human Tie2 (hTie2-Ig3-FNIII(1-3), SEQ ID NO:2) was cloned into a vector containing CMV promotor and transiently expressed by transfecting into HEK293F cell line. After 5 days of incubation, the expressed recombinant hTie2-Ig3-FNIII (1-3) protein was purified by affinity column using Protein A. Five-week-old BALB/c mice were immunized with purified hTie2-Ig3-FNIII(1-3) (100 µg/injection) mixed with an adjuvant twice weekly for 6 weeks. Anti-Tie2 antibody titers in the sera of immunized mice were examined by human Tie2 (hTie2) ELISA kit (R&D). When the antibody titer (1:5,000 dilution) suitably increased (OD>1.0), the spleens were extracted from the immunized mice, and B lymphocytes were isolated therefrom and fused with cultured myeloma cells (SP2/0). The fused cells were cultured in a HAT medium containing hypoxanthine, aminopterin and thymidine, and hybridoma cells comprised only of a fusion of myeloma cells and B lymphocytes were selected therefrom and cultured. Survived hybridoma cells were seeded in 96-well plates and the culture supernatants were tested by hTie2 ELISA. Hybridoma pools showing a positive signal were selected for clonal selection through limiting dilution. Finally, 37 monoclonal hybridoma lines were established. Among them, several Tie2-binding antibodies showed Tie2-activating activity. Candidate antibodies were selected based on Tie2 activating level and high affinity against human Tie2, later processed for humanization.

TABLE 1

| Human Tie2 full-length (hTie2) and Ig3-FNIII(1-3) sequences |
|---|
| Human Tie2 full-length (SEQ ID NO: 1) |
| MDSLASLVLCOVSLLLSGTVEGAMDLILINSLPLVSDAETSLTCIASGWR    50 |
| PHEPITIGRDFEALMNQHQDPLEVTQDVTREWAKKVVWKREKASKINGAY    100 |

TABLE 1-continued

Human Tie2 full-length (hTie2) and Ig3-FNIII(1-3) sequences

| | |
|---|---|
| FCEGRVRGEAIRIRTMKMRQQASFLPATLTMTVDKODNVNISFKKVLIKE | 150 |
| EDAVIYKNGSFIHSVPRHEVPDILEVHLPHAQPQDAGVYSARYIGGNLFT | 200 |
| SAFTRLIVRRCEAQKWGPECNHLCTACMNNOVCHEDTGECICPPGFMGRT | 250 |
| CEKACELHTFORTCKERCSGQEOCKSYVFCLPDPYGCSCATGWKOLQCNE | 300 |
| ACHPGFYGPDCKLRCSCNNGEMCDRFQGCLCSPOWQGLQCEREGIQRMTP | 350 |
| KIVDLPDHIEVNSOKFNPICKASGWPLPTNEEMTLVKPDGTVLHPKDFNH | 400 |
| TDHFSVAIFTIHRILPPDSGVWVCSVNTVAGMVEKPFNISVKVLPKPLNA | 450 |
| PNVIDTGHNFAVINISSEPYFGDGPIKSKKLLYKPVNHYEAWQHIQVTNE | 500 |
| IVTLNYLEPRTEYELCVQLVRRGEGGEGHPGPVRRFTTASIGLPPPROLN | 550 |
| LLPKSQTTLNLTWQPIFPSSEDDFYVEVERRSVQKSDQQNIKVPONLTSV | 600 |
| LLNNLHPREQYVVRARVNTKAQGEWSEDLTAWTLSDILPPQPENIKISNI | 650 |
| THSSAVISWTILDGYSISSITIRYKVQGKNEDQHVDVKIKNATITQYQLK | 700 |
| GLEPETAYQVDIFAENNIGSSNPAFSHELVTLPESQAPADLOGGKMLLIA | 750 |
| ILGSAGMTCLTVLLAFLIILQLKRANVQRRMAQAFQNVREEPAVQFNSGT | 800 |
| LALNRKVKNNPDPTIYPVLDWNDIKFQDVIGEGNFGQVLKARIKKDOLRM | 850 |
| DAAIKRMKEYASKDDHRDFAGELEVLCKLGHHPNIINLLGACEHRGYLYL | 900 |
| AIEYAPHONLLDFLRKSRVLETDPAFAIANSTASTLSSQQLLHFAADVAR | 950 |
| GMDYLSQKQFIHRDLAARNILVGENYVAKIADFOLSRGQEVYVKKTMGRL | 1000 |
| PVRWMAIESLNYSVYTTNSDVWSYGVLLWEIVSLOGTPYCGMTCAELYEK | 1050 |
| LPQGYRLEKPLNCDDEVYDLMRQCWREKPYERPSFAQILVSLNRMLEERK | 1100 |
| TYVNTTLYEKFTYAGIDCSAEEAA | 1124 |
| Human Tie2 Ig3-FNIII(1-3) (SEQ ID NO: 2) | |
| TPKIVDLPDHIEVNSOKFNPICKASGWPLPTNEEMTLVKPDF | 50 |
| NHTDHFSVAIFTIHRILPPDSGVWVCSVNTVAGMVEKPFNISVKVLPKPL | 100 |
| NAPNVIDTGHNFAVINISSEPYFGDGPIKSKKLLYKPVNHYEAWQHIQVT | 150 |
| NEIVTLNYLEPRTEYELCVQLVRRGEGGEGHPGPVRRFTTASIGLPPPRG | 200 |
| LNLLPKSQTTLNLTWQPIFPSSEDDFYVEVERRSVQKSDQQNIKVPONLT | 250 |
| SVLLNNLHPREQYVVRARVNTKAQGEWSEDLTAWTLSDILPPQPENIKIS | 300 |
| NITHSSAVISWTILDGYSISSITIRYKVQGKNEDQHVDVKIKNATITQYQ | 350 |
| LKGLEPETAYQVDIFAENNIGSSNPAFSHELVTLPESQAP | 390 |

1.2 Production and Purification of Mouse Monoclonal Anti-Tie2 Antibodies

In order to produce the anti-Tie2 antibodies selected based on the ELISA positive signals, hybridoma cells were cultured in 10% FBS-containing DMEM (Dulbecco's Modified Eagle's Medium) in a T75 (75 cm² area) flask. When the confluency of the cells reached about 90%, the cells were washed with PBS, incubated with 50 ml of serum-free medium (SFM, Gibco) and cultured at 37° C. for 3 days. Then, the culture medium in which the antibody was secreted from each monoclonal hybridoma was collected, centrifuged to remove the cells, and the culture supernatant was collected and filtered. The antibody was then purified using an AKTA purification device (GE Healthcare) equipped with a Protein G affinity column (GE Healthcare). The purified antibody was concentrated by substituting the supernatant with PBS using a centrifugal filter unit (Amicon).

1.3. Identification and Screening of Agonistic Tie2 Antibodies

To investigate whether the mouse anti-Tie2 antibodies induce the downstream signaling of the Tie2 receptor in endothelial cells, HUVECs (Lonza) were treated with an anti-Tie2 antibodies, and then the level of Akt phosphorylation, the main downstream signaling protein of Tie2 receptor, was analyzed by immunoblotting. As a positive control, COMP-Ang1 (CA1) was treated into the cells.

Specifically, HUVECs ($1\times10^5$ cells/ml) were cultured in EGM-2 medium (Lonza) at 37° C. in a 60 mm culture dish. Cells at 90% confluency were incubated with serum-free EBM-2 medium for 6 hr for serum starvation. The serum-starved HUVECs were treated with an anti-Tie2 antibodies and further incubated for 30 min. The cells were washed with cold PBS, treated with lysis buffer, and lysed at 4° C. for 20 min. Then, the cell lysates were prepared by centrifugation at 13000 rpm for 15 min. By adding 5×SDS sample buffer, cell lysate were prepared and the cell lysates were subjected to SDS PAGE and proteins were transferred to a nitrocellulose membrane (GE).

To investigate Akt phosphorylation, the blot was blocked with 5% skim milk-containing TBS-T at room temperature (RT) for 1 hr, and incubated with anti-phospho-Akt antibody (S473) at 4° C. for about 8 hr. The signals of phospho-Akt were visualized by an enhanced chemiluminescence (ECL). Then, the membrane was incubated in a stripping buffer (Thermo) for 15 min, and then reprobed with an anti-Akt antibody to determine the amount of total Akt.

Akt phosphorylation at S473 was strongly induced in several groups treated with an anti-Tie2 antibody such as 11C4, 4A4, 3B2, 3E12 and 3H7 (FIG. 1).

1.4. Affinity Measurement of Anti-Tie2 Antibodies Against hTie2 by Octet Analysis The affinity of mouse monoclonal antibody against hTie2 was measured using Octet system (ForteBio) where Black 96-well plates (96 well F-type black plates, Greiner) were used. The biosensor used for affinity measurements was hydrated for 10 min before measurement with AR2G tip (ForteBio Octet). After the hydration, hTie2 was diluted in 10 mM sodium acetate, pH 6.0 buffer at a concentration of 10 μg/ml, fixed on AR2G biosensor, and blocked with 1M ethanolamine. The mouse monoclonal anti-Tie2 antibodies were diluted to 50, 25, 12.5, 6.25, 3.125, and 0 nM with 1× kinetic buffer, and subjected to association for 300 seconds and dissociation for 900 seconds. For affinity measurement ($K_D$), the association rate (K-on) and dissociation rate (K-off) were analyzed by binding curve (global) and fitted to 1:1 binding model using Octet data analysis v9.0.0.10 program. The affinities of mouse anti-Tie2 antibodies are shown in Table 2.

TABLE 2

Affinities to hTie2 of mouse anti-Tie2 antibodies

| Antibody | Kon (1/Ms) | Koff (1/s) | $K_D$ (M) |
| --- | --- | --- | --- |
| 11C4 | 1.52E+06 | 3.27E−04 | 2.15E−10 |
| 4A4 | 5.25E+05 | 5.53E−05 | 1.05E−10 |
| 3B2 | 4.44E+05 | <1.0E−07 | <1.0E−12 |
| 3E12 | 3.63E+05 | 9.12E−05 | 2.51E−10 |
| 3H7 | 3.84E+05 | 2.13E−05 | 5.56E−11 |

1.5. Tie2 Phosphorylation Induced by Mouse Tie2 Antibody 3H7

The anti-Tie2 antibodies developed in this invention are shown to bind and induce Tie2 clustering, ultimately triggering Tie2 activation. Experiments were conducted to analyze the effect of anti-Tie2 antibody on Tie2 phosphorylation using HUVECs.

Specifically, HUVECs (Lonza) were cultured in EGM-2 (Lonza) at 37° C. and 5% $CO_2$ concentration in a 100 mm culture dish. At 80-90% confluency, the cells were changed to EBM-2 (Lonza) medium for 6 hr for serum starvation. Anti-Tie2 antibody at various concentrations (0.02 μg/ml to 50 μg/ml) were treated on the cultured cells and further incubated for 30 min. The cells were washed twice with cold PBS, lysed in 1000 μl of lysis buffer (10 mM Tris-Cl pH 7.4, 150 mM NaCl, 5 mM EDTA, 10% glycerol, 1% Triton X-100, protease inhibitor, phosphatase inhibitor) and then incubated at 4° C. for 60 min. Cell extracts were prepared and centrifuged at 12,000 rpm for 10 min. Protein concentration in the supernatant was quantitated by BCA assay.

For Tie2 immunoprecipitation, 1 μg of Tie2 antibody (R&D systems, AF313) was added into 0.5 mg of lysates and incubated overnight at 4° C. with shaking. Then, Dynabeads™ Protein G (Life technologies) was added to react for 2 hrs. The beads were immobilized on one side of the tube using a magnet, washed three times with lysis buffer, and then incubated at 70° C. for 10 min with 2×SDS sample buffer containing reducing agent. The beads were removed from the sample and electrophoresed on a 4-15% SDS protein gel (Bio-Rad) and then transferred to a 0.45 μm PVDF membrane.

Figure 2:
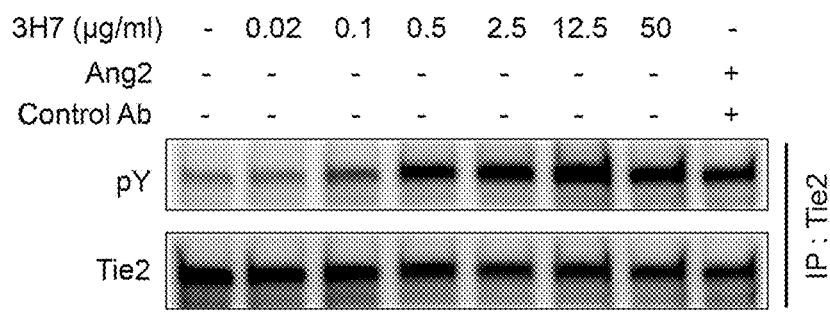
FIG. 2 shows analysis of dose-dependent Tie2 phosphorylation (pTie2) triggered by anti-Tie2 antibody 3H7. The capability of 3H7 antibody to induce Tie2 phosphorylation was investigated by immunoprecipitation and Western blotting analysis. Serum-starved HUVECs were incubated for 30 min with various concentrations of 3H7 antibody. As a control, HUVECs were incubated with Ang2/control Ab mixture. The cell lysates were subjected to immunoprecipitation with anti-Tie2 antibody, followed by SDS-PAGE/Western blotting analysis. Tie2 phosphorylation was probed by mouse anti-phospho-tyrosine (pY) antibody 4G10.

The membrane was blocked with TBS-T mixed with 5% (v/v) BSA at room temperature for 1 hr and incubated with anti-phospho tyrosine antibody (4G10, Millipore) at 4° C. for 8 hr, followed by the incubation of HRP-conjugated anti-mouse antibody and subsequent Western blotting analysis. To measure the amount of immunoprecipitated Tie2, the membrane was reacted in a stripping buffer (Thermo) for 15 min, then blocked again and reprobed with anti-Tie2 antibody (R&D systems, AF313). As shown in FIG. 2, when the anti-Tie2 antibody 3H7 was added to the HUVEC cells, the phosphorylation of Tie2 was strongly induced in a dose-dependent manner. These data indicate that the anti-Tie2 antibody 3H7 directly induce the activation of Tie2 receptor in human endothelial cells.

1.6. Clustered-Tie2 Endocytosis and FOXO1 Translocation in HUVECs by Tie2 Antibody (3H7)

The effect of 3H7 on the Tie2 localization and FOXO1 translocation from nucleus to cytosol was examined in HUVECs by immunofluorescence. Specifically, HUVECs were seeded on 8 well slide chamber (Lab-TekII) and maintained in EGM-2 medium for 2-3 days. At 100% confluence, the cells were serum staved with EBM-2 medium for 4 hr and then treated with 1 μg/ml of anti-Tie2 antibody 3H7 for 30 min. Thereafter, the cells were fixed with 4% formaldehyde in PBS at room temperature (RT) for 10 min, permeabilized with 0.1% Triton X-100 in PBS, blocked with 1% BSA in PBS at RT for 60 min, and incubated with primary antibodies at RT for 1 hr. The primary antibodies for hTie2 and FOXO1 were used. The cells were then incubated with secondary antibodies (Invitrogen) in the dark at RT for 1 hr and mounted with Vectashield mounting medium with DAPI (Vector Labs). Images were taken with a laser scanning confocal microscope (LSM880, Carl Zeiss).

Figure 3:
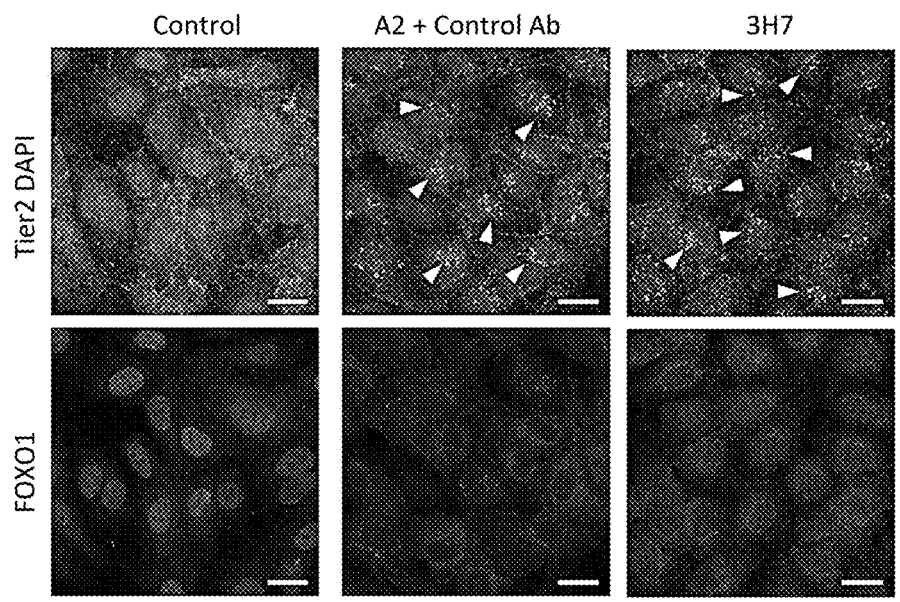
FIG. 3 shows Tie2 endocytosis and FOXO1 translocation triggered by anti-Tie2 antibody 3H7. HUVECs were serum starved for 6 hr and were incubated with 3H7, or Ang2 (A2) together with Control anti-Ang2 antibody (Control Ab, 1 ug/ml) for 30 min. After fixation, HUVECs were stained with DAPI, anti-Tie2 antibody, and anti-FOXO1 antibody to investigate the localization of clustered-Tie2 receptor, and FOX01. Arrowheads indicate the endocytosed Tie2 receptor by 3H7.

As shown in FIG. 3, the treatment of 3H7 markedly induced Tie2 endocytosis just like Control Ang2 antibody, which was known to induce Tie2 clustering and activation (Han et al., 2016, Science Translation Medicine). Consistent with a previous report showing FOXO1 localization in the cytoplasm after phosphorylation (Zhang et al, JBC 2002, 277, 45276-45284) while it was located in the nucleus under the basal, serum-starved condition, FOXO1 became markedly disappeared in nucleus with the treatment of 3H7, compared to serum-starved control.

1.7. Inhibition of Vascular Permeability Induced by VEGF or TNF-a when Treated Anti-Tie2 Antibody 3H7 in HUVECs.

Vascular leakage assay was carried out in HUVECs using In Vitro Vascular Permeability Assay Kit (Millipore) according to the manufacturer's instruction. HUVECs were seeded into the insert of the transwell plate and cultured for 3 days for 100% confluence. The HUVECs were pre-incubated with Ang2 (1 µg/ml), Ang2 (1 µg/ml) together with control antibody (1 µg/ml), or 3H7 antibody (1 µg/ml) alone for 30 min, and then VEGF (500 ng/ml) or TNF-a (100 ng/ml) was added, and the cells were incubated at 37° C. for 45 min or 22 hr, respectively. FITC-dextran was added to the upper chamber and incubated for 20 min. Passage of FITC-dextran though the HUVEC monolayer was measured by a fluorescence reader at excitation and emission wavelengths of 485 and 535 nm, respectively. As shown in FIG. 4, pre-treatment of anti-Tie2 antibody 3H7 significantly inhibited the vascular leakage induced by vascular-leakage promoting factor VEGF or TNF-a.

Example 2

DNA Gene Sequence Analysis of Mouse Anti-Tie2 Antibodies

The DNA base sequences of the antibodies (derived from hybridoma cells) selected in Example 1.3 were analyzed. Specifically, hybridoma cells ($2\times10^6$ cells/ml) were cultured in 10% FBS-containing DMEM and then total RNA was obtained using RNeasy mini kit (Qiagen). Next, RNA concentration was measured, and cDNA was synthesized through reverse transcription (RT) reaction. To amplify the heavy and light chain variable region gene sequences, PCR was carried out using Mouse Ig-Primer set (Novagen) under the following conditions using above cDNA as a template: 94° C. 5 min; [1 min at 94° C., 1 min at 50° C., 2 min at 72° C.]×35 cycles; 6 min at 72° C.; cooling to 4° C. The PCR product obtained from each reaction was cloned into a TA vector, and subjected to DNA sequencing, thereby obtaining the base sequences encoding the CDR, heavy-chain variable region and light-chain variable region of each antibody (Tables 3 to 12).

TABLE 3

| CDR sequence of mouse anti-Tie2 antibody 3B2 | | |
|---|---|---|
| Antibody | CDR Sequence | |
| 3B2 | Heavy Chain CDR Sequence | |
| | CDRH1-KABAT<br>SYWMN<br>(SEQ ID NO: 3) | CDRH2-KABAT<br>MIHPSDSETRLNQKFKD<br>(SEQ ID NO: 4) | CDRH3-KABAT<br>GNYFDC<br>(SEQ ID NO: 5) |
| | Light Chain CDR Sequence | |
| | CDRL1-KABAT<br>RASQDIGISLN<br>(SEQ ID NO: 6) | CDRL2-KABAT<br>ATSILDS<br>(SEQ ID NO: 7) | CDRL3-KABAT<br>LQYASSPWT<br>(SEQ ID NO: 8) |

TABLE 4

| Variable region sequence of mouse anti-Tie2 antibody 3B2 |
|---|
| Antibody    Variable Region Sequence |
| 3B2    Heavy Chain Variable Region Sequence |
| QVQLQQPGAELVRPGASVKLSCKASGYSFTSYWMNWVKQRPGQGLEWIGMIHPS<br>DSETRLNQKFKDKATLTVDKSSSTAYLQLSSPTSEDSAVYYCARGNYFDCWGQG<br>TTLTVSS<br>(SEQ ID NO: 9)<br>CAGGTCCAACTGCAGCAGCCTGGGGCTGAGCTGGTGAGGCCTGGAGCTTCAGT<br>GAAGCTGTCCTGCAAGGCTTCTGGCTACTCCTTCACCAGCTACTGGATGAACTG<br>GGTGAAGCAGAGGCCTGGACAAGGCCTTGAGTGGATTGGCATGATTCATCCTTC<br>CGATAGTGAAACTAGGTTAAATCAGAAGTTCAAGGACAAGGCCACATTGACTGT<br>AGACAAATCCTCCAGCACAGCCTACTTGCAACTCAGCAGCCCGACATCTGAGGA<br>CTCTGCGGTCTATTACTGTGCAAGGGGGAACTACTTTGACTGCTGGGGCCAAGG<br>CACCACTCTCACAGTCTCCTCA<br>(SEQ ID NO: 10) |
| Light Chain Variable Region Sequence |
| DIQMTQSPSSLSASLGERVSLTCRASQDIGISLNWLQQEPDGTIKRLIYATSILDSGV<br>PKRFSGSRSGSDYSLTISSLESEDFVDYYCLQYASSPWTFGGGTKLEIK<br>(SEQ ID NO: 11)<br>GACATCCAGATGACCCAGTCTCCATCCTCCTTATCTGCCTCTCTGGGAGAAAGGG<br>TCAGTCTCACTTGTCGGGCAAGTCAGGACATTGGTATTAGCTTAAACTGGCTTCA |

TABLE 4-continued

Variable region sequence of mouse anti-Tie2 antibody 3B2

| Antibody | Variable Region Sequence |
|---|---|
| | GCAGGAACCAGATGGAACTATTAAACGCCTGATCTACGCCACATCCATTTTAGAT<br>TCTGGTGTCCCCAAAAGGTTCAGTGGCAGTAGGTCTGGGTCAGATTATTCTCTCA<br>CCATCAGCAGCCTTGAGTCTGAAGATTTTGTAGACTATTACTGTCTACAATATGCT<br>AGTTCTCCGTGGACGTTCGGTGGAGGCACCAAGCTGGAAATCAAA<br>(SEQ ID NO: 12) |

TABLE 5

CDR sequence of mouse anti-Tie2 antibody 3E12

| Antibody | CDR Sequence | | |
|---|---|---|---|
| 3E12 | Heavy Chain CDR Sequence | | |
| | CDRH1-KABAT<br>SYWMN<br>(SEQ ID NO: 13) | CDRH2-KABAT<br>MIHPSDSETRLNQKFKD<br>(SEQ ID NO: 14) | CDRH3-KABAT<br>GYYFGY<br>(SEQ ID NO: 15) |
| | Light Chain CDR Sequence | | |
| | CDRL1-KABAT<br>RASQDIGISLN<br>(SEQ ID NO: 16) | CDRL2-KABAT<br>ATSNLDS<br>(SEQ ID NO: 17) | CDRL3-KABAT<br>LQYASSPPT<br>(SEQ ID NO: 18) |

TABLE 6

Variable region sequence of mouse anti-Tie2 antibody 3E12

| Antibody | Variable Region Sequence |
|---|---|
| 3E12 | Heavy Chain Variable Region Sequence |
| | QVQLQQPGADLVRPGASVKLSCKASGYSFTSYWMNWVKQRPGQGLEWIGMIHPS<br>DSETRLNQKFKDKATLTVDKSSSTAYMQLSSPTSEDSAVYYCAKGYYFGYWGQ<br>GTTLTVSS<br>(SEQ ID NO: 19)<br>CAGGTCCAACTGCAGCAGCCTGGGGCTGACCTGGTGAGGCCTGGAGCTTCAGT<br>GAAGCTGTCCTGCAAGGCTTCTGGCTACTCCTTCACCAGCTACTGGATGAACTG<br>GGTGAAGCAGAGGCCTGGACAAGGCCTTGAGTGGATTGGCATGATTCATCCTTC<br>CGATAGTGAAACTAGGTTAAATCAGAAGTTCAAGGACAAGGCCACATTGACTGT<br>AGACAAATCCTCCAGCACAGCCTACATGCAACTCAGCAGCCCGACATCTGAGGA<br>CTCTGCGGTCTATTACTGTGCAAAGGGGTACTACTTTGGCTACTGGGGCCAAGGC<br>ACCACTCTCACAGTCTCCTCA<br>(SEQ ID NO: 20) |
| | Light Chain Variable Region Sequence |
| | DIQMTQSPSSLSASLGERVSLTCRASQDIGISLNWLQQEPDGTIKRLIYATSNLDSG<br>VPKRFSGSRSGSDYSLTISSLESEDFVDYYCLQYASSPPTFGGGTKLEIK<br>(SEQ ID NO: 21)<br>GACATCCAGATGACCCAGTCTCCATCCTCCTTATCTGCCTCTCTGGGAGAAAGAG<br>TCAGTCTCACTTGTCGGGCAAGTCAGGACATTGGTATTAGTTTAAACTGGCTTCA<br>GCAGGAACCAGATGGAACTATTAAACGCCTGATCTACGCCACATCCATTTAGAT<br>TCTGGTGTCCCCAAAAGGTTCAGTGGCAGTAGGTCTGGGTCAGATTATTCTCTCA<br>CCATCAGCAGCCTTGAGTCTGAAGATTTTGTAGACTATTACTGTCTACAATATGCT<br>AGTTCTCCTCCGACGTTCGGTGGAGGCACCAAGCTGGAAATCAAA<br>(SEQ ID NO: 22) |

TABLE 7

CDR sequence of mouse anti-Tie2 antibody 3H7

| Antibody | CDR Sequence | | |
|---|---|---|---|
| 3H7 | Heavy Chain CDR Sequence | | |
| | CDRH1-KABAT<br>SYWMN<br>(SEQ ID NO: 23) | CDRH2-KABAT<br>MIHPSDSETRLNQKFMD<br>(SEQ ID NO: 24) | CDRH3-KABAT<br>GLYGNS<br>(SEQ ID NO: 25) |

TABLE 7-continued

CDR sequence of mouse anti-Tie2 antibody 3H7

| Antibody | CDR Sequence | | |
|---|---|---|---|
| | Light Chain CDR Sequence | | |
| | CDRL1-KABAT<br>RASQDIGISLN<br>(SEQ ID NO: 26) | CDRL2-KABAT<br>ATSSLDS<br>(SEQ ID NO: 27) | CDRL3-KABAT<br>LQYASSPYT<br>(SEQ ID NO: 28) |

TABLE 8

Variable region sequence of mouse anti-Tie2 antibody 3H7

| Antibody | Variable Region Sequence |
|---|---|
| 3H7 | Heavy Chain Variable Region Sequence |

QVQLQQPGAELVRPGASVKLSCKASGYSFTSYWMNWVKQRPGQGLEWIG**MIHPS
DSETRLNQKFMD**KATLTVDKSSSTAYMQLSSPTSEDSAVYYCARGLYGNSWGQ
GTLVTVSA
(SEQ ID NO: 29)
CAGGTCCAACTGCAGCAGCCTGGGGCTGAGCTGGTGAGGCCTGGAGCTTCAGT
GAAGCTGTCCTGCAAGGCTTCTGGCTACTCCTTCACCAGCTACTGGATGAACTG
GGTGAAGCAGAGGCCTGGACAAGGCCTTGAGTGGATTGGCATGATTCATCCTTC
CGATAGTGAAACTAGGTTAAATCAGAAGTTCATGGACAAGGCCACATTGACTGT
AGACAAATCCTCCAGCACAGCCTACATGCAGCTCAGCAGCCCGACATCTGAGGA
CTCTGCGGTCTATTACTGTGCTCGTGGCCTCTATGGTAACTCTTGGGGCCAAGGG
ACTCTGGTCACTGTCTCTGCA
(SEQ ID NO: 30)

Light Chain Variable Region Sequence

DIQMTQSPSSLSASLGERVSLTCRASQDIGISLNWLQQEPDGTIKRLIYATSSLDSG
VPKRFSGSRSGSDYSLTISSLESEDFVDYYCLQYASSPYTFGGGTKLEIK
(SEQ ID NO: 31)
GACATCCAGATGACCCAGTCTCCATCCTCCTTATCTGCCTCTCTGGGAGAAAGAG
TCAGTCTCACTTGTCGGGCAAGTCAGGACATTGGTATTAGCTTAAACTGGCTTCA
GCAGGAACCAGATGGAACTATTAAACGCCTGATCTACGCCACATCCAGTTTAGAT
TCTGGTGTCCCCAAAAGGTTCAGTGGCAGTAGGTCTGGGTCAGATTATTCTCTCA
CCATCAGCAGCCTTGAGTCTGAAGATTTTGTAGACTATTACTGTCTACAATATGCT
AGTTCTCCGTACACGTTCGGAGGGGGGACCAAGCTGGAAATAAAA
(SEQ ID NO: 32)

TABLE 9

CDR sequence of mouse anti-Tie2 antibody 4A4

| Antibody | CDR Sequence | | |
|---|---|---|---|
| 4A4 | Heavy Chain CDR Sequence | | |
| | CDRH1-KABAT<br>SYWMN<br>(SEQ ID NO: 33) | CDRH2-KABAT<br>MIHPSDSETRLNQKFKD<br>(SEQ ID NO: 34) | CDRH3-KABAT<br>GYYFDY<br>(SEQ ID NO: 35) |
| | Light Chain CDR Sequence | | |
| | CDRL1-KABAT<br>RASQDIGISLN<br>(SEQ ID NO: 36) | CDRL2-KABAT<br>ATSSLDS<br>(SEQ ID NO: 37) | CDRL3-KABAT<br>LQYVSSPWT<br>(SEQ ID NO: 38) |

TABLE 10

Variable region sequence of mouse anti-Tie2 antibody 4A4

| Antibody | Variable Region Sequence |
|---|---|
| 4A4 | Heavy Chain Variable Region Sequence |

QVQLQQPGAELVRPGASVKLSCKASGYSFTSYWMNWVKQRPGQGLEWIG**MIHPS

TABLE 10-continued

Variable region sequence of mouse anti-Tie2 antibody 4A4

| Antibody | Variable Region Sequence |
| --- | --- |
| | DSETRLNQKFKDKATLTVDKSSSTAYMQLSSPTSEDSAVYYCARGYYFDYWGQG<br>TTLTVSS<br>(SEQ ID NO: 39)<br>CAGGTCCAACTGCAGCAGCCTGGGGCTGAGCTGGTGAGGCCTGGAGCTTCAGT<br>GAAGCTGTCCTGCAAGGCTTCTGGCTACTCCTTCACCAGCTACTGGATGAACTG<br>GGTGAAGCAGAGGCCTGGACAAGGCCTTGAGTGGATTGGCATGATTCATCCTTC<br>CGATAGTGAAACTAGGTTAAATCAGAAGTTCAAGGACAAGGCCACATTGACTGT<br>AGACAAATCCTCCAGCACAGCCTACATGCAACTCAGCAGCCCGACATCTGAGGA<br>CTCTGCGGTCTATTACTGTGCAAGAGGCTACTACTTTGACTACTGGGGCCAAGGC<br>ACCACTCTCACAGTCTCCTCA<br>(SEQ ID NO: 40) |
| | Light Chain Variable Region Sequence |
| | DIQMTQSPSSLSASLGERVSLTCRASQDIGISLNWLQQEPDGTIKRLIYATSSLDSG<br>VPKRFTGSRSGSDYSLTISSLESEDFVDYYCLQVSSPWTFGGGTKLEIK<br>(SEQ ID NO: 41)<br>GACATCCAGATGACCCAGTCTCCATCCTCCTTATCTGCCTCTCTGGGAGAAAGAG<br>TCAGTCTCACTTGTCGGGCAAGTCAGGACATTGGTATTAGCTTAAACTGGCTTCA<br>GCAGGAACCAGATGGAACTATTAAACGCCTGATCTACGCCACATCCAGTTTAGAT<br>TCTGGTGTCCCCAAGAGGTTCACTGGCAGTAGGTCTGGGTCAGATTATTCTCTCA<br>CCATCAGCAGCCTTGAGTCTGAAGATTTTGTAGACTATTACTGTCTACAATATGTT<br>AGTTCTCCGTGGACGTTCGGTGGAGGCACCAAGCTGGAAATCAAA<br>(SEQ ID NO: 42) |

TABLE 11

CDR sequence of mouse anti-Tie2 antibody 11C4

| Antibody | CDR Sequence | | |
| --- | --- | --- | --- |
| 11C4 | Heavy Chain CDR Sequence | | |
| | CDRH1-KABAT<br>SYWMN<br>(SEQ ID NO: 43) | CDRH2-KABAT<br>MIHPSDSETRLNQKFKD<br>(SEQ ID NO: 44) | CDRH3-KABAT<br>LTIYFDY<br>(SEQ ID NO: 45) |
| | Light Chain CDR Sequence | | |
| | CDRL1-KABAT<br>RASQDIGISLN<br>(SEQ ID NO: 46) | CDRL2-KABAT<br>ATSSLDS<br>(SEQ ID NO: 47) | CDRL3-KABAT<br>LQYASSPYT<br>(SEQ ID NO: 48) |

TABLE 12

Variable region sequence of mouse anti-Tie2 antibody 11C4

| Antibody | Variable Region Sequence |
| --- | --- |
| 11C4 | Heavy Chain Variable Region Sequence |
| | QVQLQQPGADLVRPGASVTLSCKASGYSFTSYWMNWVKQRPGQGLEWIGMIHPS<br>DSETRLNQKFKDKATLTVDKSSSTAYMQLRSPTSEDSAVYYCAGLTIYFDYWGQ<br>GTTLTVSS<br>(SEQ ID NO: 49)<br>CAGGTCCAACTACAGCAGCCTGGGGCTGACCTGGTGAGGCCTGGAGCTTCAGT<br>GACGCTGTCCTGCAAGGCTTCTGGCTACTCCTTCACCAGCTACTGGATGAACTG<br>GGTGAAGCAGAGGCCTGGACAAGGCCTGGAGTGGATTGGCATGATTCATCCTTC<br>CGATAGTGAAACTAGGTTAAATCAGAAGTTCAAGGACAAGGCCACATTGACTGT<br>AGACAAATCCTCCAGCACAGCCTACATGCAACTCCGCAGCCCGACATCTGAGGA<br>CTCTGCGGTCTATTACTGTGCAGGCCTAACTATTTACTTTGACTATTGGGGCCAAG<br>GCACCACTCTCACAGTCTCCTCA<br>(SEQ ID NO: 50) |
| | Light Chain Variable Region Sequence |
| | DIQMTQSPSSLSASLGERVSLTCRASQDIGISLNWLQQEPDGTIKRLIYATSSLDSG<br>VPKRFSGSRSGSDYSLTISSLESEDFVDYYCLQYASSPYTFGGGTKLEIK<br>(SEQ ID NO: 51)<br>GACATCCAGATGACCCAGTCTCCATCCTCCTTATCTGCCTCTCTGGGAGAAAGAG |

TABLE 12-continued

Variable region sequence of mouse anti-Tie2 antibody 11C4

| Antibody | Variable Region Sequence |
|---|---|
| | TCAGTCTCACTTGTCGGGCAAGTCAGGACATTGGTATTAGCTTAAACTGGCTTCA<br>GCAGGAACCAGATGGAACTATTAAACGCCTGATCTACGCCACATCCAGTTTAGAT<br>TCTGGTGTCCCCAAAAGGTTCAGTGGCAGTAGGTCTGGGTCAGATTATTCTCTCA<br>CCATCAGCAGCCTTGAGTCTGAAGATTTTGTAGACTATTACTGTCTACAATATGCT<br>AGTTCTCCGTACACGTTCGGAGGGGGGACCAAGCTGGAAATAAAA<br>(SEQ ID NO: 52) |

Example 3

Epitope Mapping of Mouse Anti-Tie2 Antibody Against hTie2

The antigenic determinants (epitopes) of hTie2 recognized by mouse monoclonal antibody 3H7 was analyzed by HDX-MS (Hydrogen/deuterium exchange-mass spectrometry) technique. HDX-MS analysis methods are described in the following articles; Houde D, Engen J R (2013) Methods Mol. Biol. 988: 269-89 and Houde et al. (2011) J. Pharm. Sci. 100 (6), 2071.

Recombinant hTie2-Ig3-FNIII(1-3) protein was used to analyze the binding-epitopes of antibody 3H7. Before deuterium labeling reaction, hTie2-Ig3-FNIII(1-3)/antibody mixture was incubated for more than 3 hrs to be maintained to the maximum binding (100%) under 15× diluted deuterium labeling buffer ($K_D$=25 nM). The prepared hTie2-Ig3-FNIII(1-3)/antibody complex was diluted 15 times with deuterium labeling buffer, labeled at various time, and then quenched with the same volume of quenching buffer. The labeling reaction time was 0 min (undeuterium), 0.33 min, 10 min, 60 min and 240 min. However, in undeuterium condition, the deuterium labeling buffer was replaced with equilibrium buffer and the reaction was immediately stopped with quenching buffer. For mass spectrometry, the deuterium labeled hTie2-Ig3-FNIII(1-3)/antibody sample was loaded on a pepsin column and peptide digestion was carried out. Mass spectrometry analysis showed that 82.6% coverage data is obtained from a total of 50 peptic peptides.

The deuterium uptake difference between hTie2-Ig3-FNIII(1-3) alone and hTie2-Ig3-FNIII (1-3)/antibody complex conditions was comparatively analyzed, and a region showing a distinct decrease in the deuterium uptake is either a peptide to which the antibody binds directly, or a structurally changed region. When the deuterium uptake difference between hTie2-Ig3-FNIII(1-3) alone and the hTie2-Ig3-FNIII(1-3)/antibody complex was 0.5-1 Da or more, it was considered significant, indicated as bold in Table 13.

Figure 6:
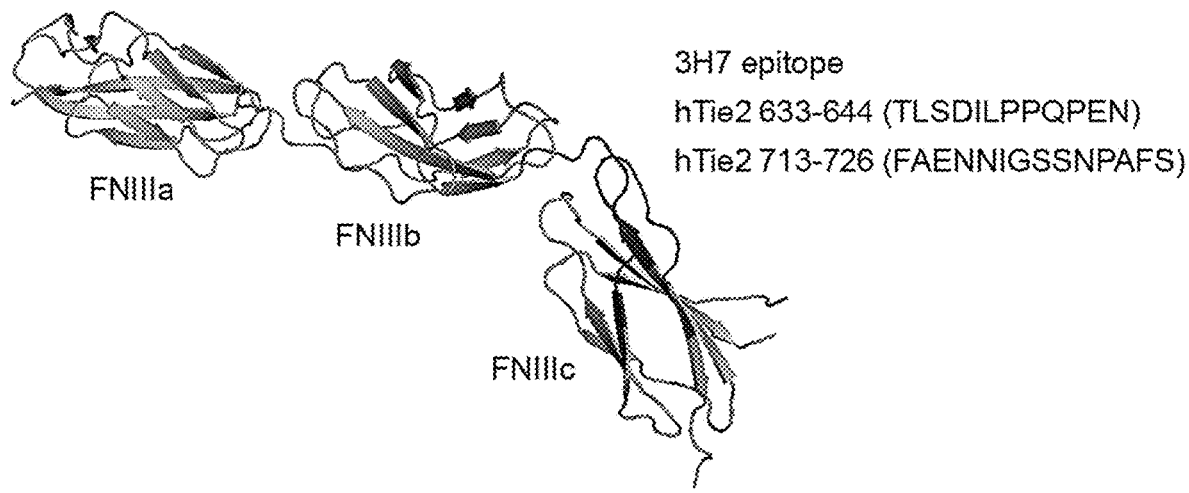
FIG. 6 is the schematic showing 3H7-binding epitope on Tie2. Anti-Tie2 antibody 3H7-binding epitope (black) on the FNIIIc of the hTie2 antigen, analyzed by H/D exchange-mass spectrometry, was visualized in the image of hTie2 FNIII(1-3) crystal structure (PDB: 5UTK) using PyMol™ software. The sequences shown in FIG. 6 are residues 633 to 644 of SEQ ID NO: 1 (TLSDILPPQPEN) and residues 713-726 of SEQ ID NO: 1 (FAENNIGSSNPAFS).

Heat map of deuterium uptake per residue at 0.333, 10, 60, and 240 min for hTie2 antigen was generated in the absence or presence of anti-Tie2 antibody 3H7 using the data of H/D exchange-mass spectrometry (FIG. 5). Gray scale indicates the percentage of H/D exchange per residue between the antigen alone and antigen/mAb mixture at each individual time. The heat map analysis of the deuterium uptake difference indicated that the epitopes to which antibody 3H7 binds are residues 633 to 644 (SEQ ID NO: 1, TLSDILPPQPEN) and 713-726 (SEQ ID NO: 1, FAEN-NIGSSNPAFS) of hTie2 (Table 13). The epitope was shown on the 3D structure of hTie2-FNIII, which was generated using PyMol software (FIG. 6).

TABLE 13

Epitope mapping analysis for 3H7 binding to hTie2 by HDX-MS
3117 binding to hTie2-Ig3-FNIII(1-3)

| Residues (SEQ ID NO: 2) | | | Exposure Time | Relative Uptake (Da) | | |
|---|---|---|---|---|---|---|
| Start | End | Sequence | (min) | hTie2 alone | hTie2 + 3H7 | Δ |
| 284 | 296 | WTLSDILPPQPEN | 0.00 | 0.00 | 0.00 | 0.00 |
| 284 | 296 | WTLSDILPPQPEN | 0.33 | 1.45 | 1.14 | 0.31 |
| 284 | 296 | WTLSDILPPQPEN | 10.00 | 3.09 | 2.62 | 0.47 |
| 284 | 296 | WTLSDILPPQPEN | 60.00 | 3.93 | 3.45 | 0.48 |
| 284 | 296 | WTLSDILPPQPEN | 240.00 | 4.50 | 3.99 | 0.51 |
| 287 | 296 | SDILPPQPEN | 0.00 | 0.00 | 0.00 | 0.00 |
| 287 | 296 | SDILPPQPEN | 0.33 | 1.31 | 0.99 | 0.33 |
| 287 | 296 | SDILPPQPEN | 10.00 | 2.79 | 2.32 | 0.48 |
| 287 | 296 | SDILPPQPEN | 60.00 | 3.20 | 2.70 | 0.51 |
| 287 | 296 | SDILPPQPEN | 240.00 | 3.49 | 2.92 | 0.57 |
| 308 | 314 | VISWTIL | 0.00 | 0.00 | 0.00 | 0.00 |
| 308 | 314 | VISWTIL | 0.33 | 0.07 | 0.07 | 0.00 |

TABLE 13-continued

Epitope mapping analysis for 3H7 binding to hTie2 by HDX-MS
3117 binding to hTie2-Ig3-FNIII(1-3)

| Residues (SEQ ID NO: 2) | | | Exposure Time | Relative Uptake (Da) | | |
|---|---|---|---|---|---|---|
| Start | End | Sequence | (min) | hTie2 alone | hTie2 + 3H7 | Δ |
| 308 | 314 | VISWTIL | 10.00 | 0.79 | 0.83 | -0.05 |
| 308 | 314 | VISWTIL | 60.00 | 1.48 | 1.56 | -0.08 |
| 308 | 314 | VISWTIL | 240.00 | 1.83 | 1.64 | 0.19 |
| 364 | 380 | IFAENNIGSSNPAFSHE | 0.00 | 0.00 | 0.00 | 0.00 |
| 364 | 380 | IFAENNIGSSNPAFSHE | 0.33 | 4.15 | 3.93 | 0.22 |
| 364 | 380 | IFAENNIGSSNPAFSHE | 10.00 | 5.31 | 4.62 | 0.70 |
| 364 | 380 | IFAENNIGSSNPAFSHE | 60.00 | 6.23 | 5.32 | 0.92 |
| 364 | 380 | IFAENNIGSSNPAFSHE | 240.00 | 7.15 | 6.15 | 1.00 |
| 365 | 380 | FAENNIGSSNPAFSHE | 0.00 | 0.00 | 0.00 | 0.00 |
| 365 | 380 | FAENNIGSSNPAFSHE | 0.33 | 4.40 | 4.21 | 0.19 |
| 365 | 380 | FAENNIGSSNPAFSHE | 10.00 | 5.42 | 5.05 | 0.37 |
| 365 | 380 | FAENNIGSSNPAFSHE | 60.00 | 6.08 | 5.60 | 0.47 |
| 365 | 380 | FAENNIGSSNPAFSHE | 240.00 | 6.81 | 6.11 | 0.70 |
| 366 | 380 | AENNIGSSNPAFSHE | 0.00 | 0.00 | 0.00 | 0.00 |
| 366 | 380 | AENNIGSSNPAFSHE | 0.33 | 4.04 | 3.69 | 0.35 |
| 366 | 380 | AENNIGSSNPAFSHE | 10.00 | 4.74 | 4.47 | 0.27 |
| 366 | 380 | AENNIGSSNPAFSHE | 60.00 | 5.35 | 5.08 | 0.27 |
| 366 | 380 | AENNIGSSNPAFSHE | 240.00 | 5.91 | 5.34 | 0.58 |
| 378 | 385 | SHELVTLP | 0.00 | 0.00 | 0.00 | 0.00 |
| 378 | 385 | SHELVTLP | 0.33 | 0.73 | 0.79 | -0.06 |
| 378 | 385 | SHELVTLP | 10.00 | 1.54 | 1.55 | -0.01 |
| 378 | 385 | SHELVTLP | 60.00 | 1.98 | 2.09 | -0.11 |
| 378 | 385 | SHELVTLP | 240.00 | 2.15 | 2.28 | -0.13 |

Example 4

Humanization of Mouse Anti-Tie2 Antibody and Full-Length IgG Conversion

To eliminate the immunogenicity of mouse anti-Tie2 antibody 3H7 when administered into human, the antibody was humanized as followings.

4.1. Heavy Chain Humanization

The human antibody heavy chain variable gene, IGHV1-46-01, showed 66% homology to the heavy chain sequence of antibody 3H7. Based on these analyses, the 3 CDR regions of the 3H7 antibody were grafted into the human antibody heavy chain variable gene IGHV1-46-01. In this process, 2 humanized heavy chain antibody genes were designed (Table 14). The grafted CDRs are underlined in protein sequence. Back mutations to mouse sequence were introduced in heavy chain genes of humanized 3H7, indicated as bold in protein sequence of Table 14.

4.2 Light Chain Humanization

The human antibody light chain variable gene, IGKV1-17-01, showed 68% homology to the light chain sequence of antibody 3H7. Based on these analyses, the 3 CDR regions of 3H7 antibody were grafted into the human antibody light chain variable gene IGKV1-17-01. 2 humanized light chain antibody genes were designed in this process (Table 14). The grafted CDRs are underlined in protein sequence. Back mutations to mouse sequence were introduced in light chain genes of humanized 3H7, indicated as bold in protein sequence of Table 14.

4.3. Humanized Gene Synthesis and Cloning to Human Full-Length IgG Antibody

The humanized variable regions of antibodies in Table 14 were cloned into the heavy chain and the light chain vector of the human IgG4 isotype backbone vectors. DNA fragments of the humanized heavy chain variable region of the antibodies (VH) were synthesized (Bioneer, Inc.) as a sequence of 'EcoRI-signal sequence-VH-NheI-CH-XhoI'. DNA fragments of the humanized light chain variable region of the antibodies (VL) were also synthesized as a sequence of 'EcoRI-signal sequence-VL-BsiWI-CL-XhoI'. The DNA fragments encoding the heavy chain and light chain were cloned into pOptiVEC™ or pcDNA™3.3 vectors, respectively.

TABLE 14

| Humanized anti-Tie2 antibodies originated from mouse 3H7 antibody | | |
|---|---|---|
| Antibody 3H7H11G4 | Antibody Sequence (VH) (Protein Sequence) QVQLVQSGAEVKKPGASVKVSCKASGYTFTSYWMNWVRQAPGQGLEWMGMIHPSDSETRLNQKFMDRVTMTRDTSTSTVYMELSSLRSEDTAVYYCARGLYGNSWGQGTLVTVSS (SEQ ID NO: 53) (Coding Nucleotide Sequence) CAGGTGCAGCTGGTCCAATCCGGGGCTGAGGTGAAGAAGCCTGGAGCATCAGTGAAAGTTTCATGCAAAGCTAGTGGTTACACCTTCACCAGCTATTGGATGAACTGGGTGCGGCAGGCCCCCGGTCAGGGGCTTGAGTGGATGGGCATGATCCACCCATCCGACTCTGAGACTAGGCTGAACCAGAAGTTTATGGATAGAGTGACCATGACAAGAGATACGTCCACTTCTACTGTCTATATGGAACTGAGCAGTCTGAGATCTGAAGACACAGCCGTTTACTACTGTGCTCGCGGACTCTATGGCAATAGCTGGGGCCAAGGAACATTGGTAACCGTCTCTTCT (SEQ ID NO: 55) | Antibody Sequence (VL) (Protein Sequence) DIQMTQSPSSLSASVGDRVTITCRASQDIGISLNWYQQKPGKAPKRLIYATSSLDSGVPSRFSGSGSGTEFTLTISSLQPEDFATYYCLQYASSPYTFGQGTKVEIK (SEQ ID NO: 54) (Coding Nucleotide Sequence) GACATCCAGATGACCCAATCTCCCTCCTCCCTGAGCGCATCCGTGGGGATAGAGTGACCATAACCTGCCGGGCCTCTCAGGACATCGGTATTTCTTTGAATTGGTATCAGCAGAAGCCCGGGAAGGCCCCTAAACGCCTGATCTATGCTACTTCCAGTCTGGACAGCGGGGTCCCGTCAAGGTTTTCAGGCAGTGGATCAGGCACAGAGTTTACACTCACAATTTCGAGCCTGCAGCCTGAAGATTTCGCCACTTATTACTGTCTTCAATACGCTAGCTCTCCATACACGTTCGGCCAGGGAACCAAGGTTGAGATTAAA (SEQ ID NO: 56) |
| 3H7H12G4 | (Protein Sequence) QVQLVQSGAEVKKPGASVKVSCKASGYTFTSYWMNWVRQAPGQGLEWMGMIHPSDSETRLNQKFMDRVTMTRDTSTSTVYMELSSLRSEDTAVYYCARGLYGNSWGQGTLVTVSS (SEQ ID NO: 57) (Coding Nucleotide Sequence) CAGGTGCAGCTGGTCCAATCCGGGGCTGAGGTGAAGAAGCCTGGAGCATCAGTGAAAGTTTCATGCAAAGCTAGTGGTTACACCTTCACCAGCTATTGGATGAACTGGGTGCGGCAGGCCCCCGGTCAGGGGCTTGAGTGGATGGGCATGATCCACCCATCCGACTCTGAGACTAGGCTGAACCAGAAGTTTATGGATAGAGTGACCATGACAAGAGATACGTCCACTTCTACTGTCTATATGGAACTGAGCAGTCTGAGATCTGAAGACACAGCCGTTTACTACTGTGCTCGCGGACTCTATGGCAATAGCTGGGGCCAAGGAACATTGGTAACCGTCTCTTCT (SEQ ID NO: 59) | (Protein Sequence) DIQMTQSPSSLSASVGDRVTITCRASQDIGISLNWLQQEPGKAPKRLIYATSSLDSGVPKRFSGSGSGTEFTLTISSLQPEDFATYYCLQYASSPYTFGQGTKVEIK (SEQ ID NO: 58) (Coding Nucleotide Sequence) GACATCCAGATGACTCAGTCCCCCTCGAGCCTCTCAGCTTCTGTTGGAGACAGAGTGACAATTACATGCCGGGCCTCACAGGATATTGGGATCTCCCTGAACTGGCTGCAACAGGAACCAGGAAAGGCCCCTAAGCGCCTGATATATGCCACATCCTCTCTTGACTCAGGGGTCCCAAAGAGGTTTAGCGGCAGTGGATCAGGTACTGAGTTCACTCTCACCATCTCTAGCCTGCAGCCTGAGGATTTTGCAACCTACTATTGTTTGCAATACGCTAGTTCCCCCTACACGTTCGGCCAGGGCACCAAAGTGGAAATCAAA (SEQ ID NO: 60) |
| 3H7H21G4 | (Protein Sequence) QVQLVQSGAEVKKPGASVKVSCKASGYTFTSYWMNWVRQRPGQGLEWIGMIHPSDSETRLNQKFMDRVTMTRDTSTSTVYMELSSLRSEDTAVYYCARGLYGNSWGQGTLVTVSS (SEQ ID NO: 61) (Coding Nucleotide Sequence) CAAGTCCAGCTCGTGCAGTCTGGCGCTGAGGTGAAAAAGCCCGGGGCCTCAGTGAAGGTTTCTTGCAAGGCAAGCGGCTACACCTTTACCTCCTATTGGATGAATTGGGTGCGACAGCGGCCAGGCCAGGGGTGGAGTGGATCGGAATGATTCACCCTAGTGACTCAGAAACTAGGCTGAACCAGAAATTCATGGACAGAGTCACAATGACGCGCGATACAAGCACTAGTACAGTTTACATGGAGCTGAGCAGCCTGAGATCGGAAGATACTGCCGTGTATTACTGTCTAGGGGACTGTATGGAAACTCTTGGGGTCAAGGCACCCTTGTAACCGTCTCTCCTCC (SEQ ID NO: 63) | (Protein Sequence) DIQMTQSPSSLSASVGDRVTITCRASQDIGISLNWYQQKPGKAPKRLIYATSSLDSGVPSRFSGSGSGTEFTLTISSLQPEDFATYYCLQYASSPYTFGQGTKVEIK (SEQ ID NO: 62) (Coding Nucleotide Sequence) GACATCCAGATGACCCAATCTCCCTCCTCCCTGAGCGCATCCGTGGGGATAGAGTGACCATAACCTGCCGGGCCTCTCAGGACATCGGTATTTCTTTGAATTGGTATCAGCAGAAGCCCGGGAAGGCCCCTAAACGCCTGATCTATGCTACTTCCAGTCTGGACAGCGGGGTCCCGTCAAGGTTTTCAGGCAGTGGATCAGGCACAGAGTTTACACTCACAATTTCGAGCCTGCAGCCTGAAGATTTCGCCACTTATTACTGTCTTCAATACGCTAGCTCTCCATACACGTTCGGCCAGGGAACCAAGGTTGAGATTAAA (SEQ ID NO: 64) |
| 3H7H22G4 | (Protein Sequence) QVQLVQSGAEVKKPGASVKVSCKA | (Protein Sequence) DIQMTQSPSSLSASVGDRVTITCRAS |

TABLE 14-continued

Humanized anti-Tie2 antibodies originated from mouse 3H7 antibody

| | |
|---|---|
| SGYTFTSYWMNWVRQRPGQGLEW<br>IGMIHPSDSETRLNQKFMDRVTMTR<br>DTSTSTVYMELSSLRSEDTAVYYCA<br>RGLYGNSWGQGTLVTVSS<br>(SEQ ID NO: 65)<br>(Coding Nucleotide Sequence)<br>CAAGTCCAGCTCGTGCAGTCTGGC<br>GCTGAGGTGAAAAAGCCCGGGGC<br>CTCAGTGAAGGTTTCTTGCAAGGC<br>AAGCGGCTACACCTTTACCTCCTAT<br>TGGATGAATTGGGTGCGACAGCGG<br>CCAGGCCAGGGGTTGGAGTGGATC<br>GGAATGATTCACCCTAGTGACTCA<br>GAAACTAGGCTGAACCAGAAATTC<br>ATGGACAGAGTCACAATGACGCGC<br>GATACAAGCACTAGTACAGTTTAC<br>ATGGAGCTGAGCAGCCTGAGATCG<br>GAAGATACTGCCGTGTATTACTGTG<br>CTAGGGGACTGTATGGAAACTCTT<br>GGGGTCAAGGCACCCTTGTAACCG<br>TCTCCTCC<br>(SEQ ID NO: 67) | QDIGISLNWLQQEPGKAPKRLIYAT<br>SSLDSGVPKRFSGSGSGTEFTLTISSL<br>QPEDFATYYCLQYASSPYTFGQGTK<br>VEIK<br>(SEQ ID NO: 66)<br>(Coding Nucleotide Sequence)<br>GACATCCAGATGACTCAGTCCCCC<br>TCGAGCCTCTCAGCTTCTGTTGGA<br>GACAGAGTGACAATTACATGCCGG<br>GCCTCACAGGATATTGGGATCTCCC<br>TGAACTGGCTGCAACAGGAACCA<br>GGAAAGGCCCCTAAGCGCCTGATA<br>TATGCCACATCCTCTCTTGACTCAG<br>GGGTCCCAAAGAGGTTTAGCGGCA<br>GTGGATCAGGTACTGAGTTCACTC<br>TCACCATCTCTAGCCTGCAGCCTG<br>AGGATTTTGCAACCTACTATTGTTT<br>GCAATACGCTAGTTCCCCCTACACG<br>TTCGGCCAGGGCACCAAAGTGGA<br>AATCAAA<br>(SEQ ID NO: 68) |

4.4. Production and Purification of Humanized Anti-Tie2 Antibodies

To produce humanized anti-Tie2 antibodies, Expi293F (Gibco) cells capable of producing recombinant proteins with high efficiency were used. Expi293F cells ($2 \times 10^6$ cells/ml) were cultured in Erlenmeyer flask, and plasmids encoding heavy chain and light chain were co-transfected into Expi293F cells with the ExpiFectamine 293 transfection kit. Cells were cultured at 37° C. under 8% $CO_2$ for 5 days in a shaking incubator (orbital shaker, 125 rpm). The resulting culture medium was collected and centrifuged to remove the cells. The culture supernatant containing secreted antibodies was isolated and stored at 4° C. or immediately purified using an AKTA purification system (GE Healthcare) equipped with an affinity column (Protein A agarose column, GE Healthcare). The purified antibody was concentrated by passing it through a protein centrifugal filter (Amicon) while the solution was replaced with PBS.

Example 5

Affinity Measurement of Humanized Anti-Tie2 Antibodies Against hTie2

The affinity of humanized anti-Tie2 antibody against hTie2 was measured using Octet system (ForteBio) where Black 96-well plates (96 well F-type black plates, Greiner) were used. The biosensor used for affinity measurements was hydrated for 10 min before measurement with AR2G tip (ForteBio Octet). After the hydration, humanized anti-Tie2 antibody was diluted in 10 mM sodium acetate, pH 6.0 buffer at a concentration of 10 μg/ml, fixed on AR2G biosensor, and blocked with 1M ethanolamine. The recombinant hTie2 was diluted to 50, 25, 12.5, 6.25, 3.125, and 0 nM with 1× kinetic buffer, and subjected to association for 300 sec and dissociation for 900 sec. For affinity measurement ($K_D$), association rate (K-on) and dissociation rate (K-off) were analyzed by binding curve (global) and fitted to 1:1 binding model using Octet data analysis v9.0.0.10 program. The $K_D$ values were shown in the following Table 15.

TABLE 15

Affinities of humanized 3H7 antibodies to hTie2-Ig3-FNIII(1-3)

| Antibody | Kon (1/Ms) | Koff (1/s) | $K_D$ (M) |
|---|---|---|---|
| 3H7 | 5.58E+05 | 1.05E−05 | 2.69E−11 |
| 3H7H11G4 | 6.26E+04 | 4.67E−04 | 7.47E−09 |
| 3H7H12G4 | 1.04E+04 | 9.99E−04 | 9.65E−08 |
| 3H7H21G4 | 7.85E+04 | 5.17E−04 | 6.59E−09 |
| 3H7H22G4 | 1.65E+04 | 6.56E−04 | 3.97E−08 |

Example 6

Analysis of In Vitro Biological Property of the Selected Humanized Anti-Tie2 Antibodies 6.1. Akt Phosphorylation To investigate whether the humanized anti-Tie2 antibodies induce the downstream signaling of the Tie2 receptor in endothelial cells, HUVECs (Lonza) were treated with humanized anti-Tie2 antibody. Then, the level of Akt phosphorylation, the main downstream signaling protein of Tie2 receptor, was measured by immunoblotting. To compare the degree of Akt activation, cells were treated with COMP-Ang1 (CA1) as a positive control in the experiment. Specifically, HUVEC cells ($1 \times 10^5$ cells/ml) were cultured in EGM-2 (Lonza) at 37° C. in 60 mm culture dish. Cells of 90% confluency were incubated with EBM-2 (Lonza) for 4 hr. The serum-starved HUVECs were treated with an anti-Tie2 antibody, and further incubated for 30 min. The cells were washed with cold PBS, treated with lysis buffer, and lysed at 4° C. for 20 min. Then, the cell lysates were prepared by centrifugation at 13000 rpm for 15 min. 5×SDS sample buffer was added to the cell lysate and the mixture was boiled at 95° C. for 5 min. Then, the mixture was subjected to SDS-PAGE and subsequent Western blotting.

To investigate the phosphorylation of Akt, the membrane was blocked with 5% skim milk-containing TBST for 1 hr at RT, and incubated with anti-phospho-Akt antibody (S473) at 4° C. for about 8 hr. The amount of phospho-Akt was visualized by enhanced chemiluminescence (ECL). Then, the membrane was incubated in a stripping buffer (Thermo)

for 15 min, and then reprobed with an anti-Akt antibody to determine the amount of total Akt.

Figure 7:
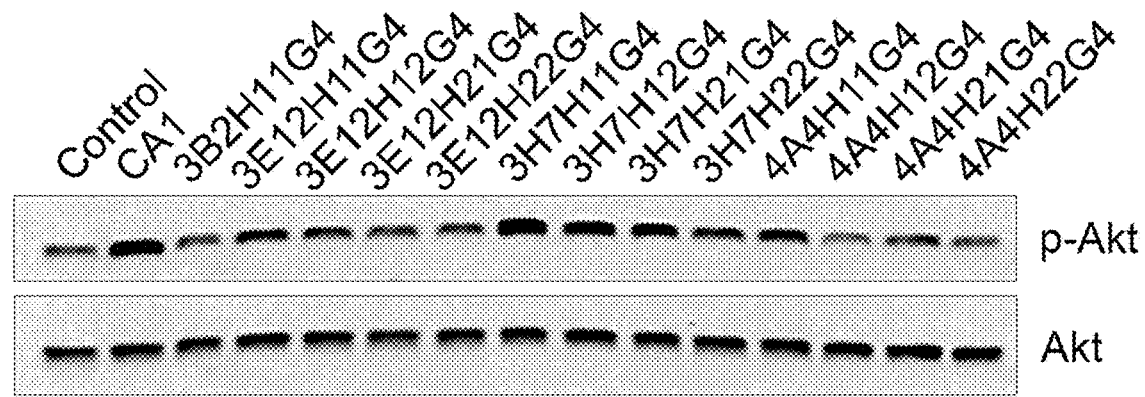
FIG. 7 shows phosphorylation of Akt (pAkt) induced by humanized anti-Tie2 antibodies. Serum-starved HUVECs were incubated for 30 min with humanized anti-Tie2 antibodies. Thereafter, the cell lysates were subjected to SDS-PAGE/Western blotting and blots were probed with anti-phospho-Akt (S473) or anti-Akt antibody.

As shown in FIG. 7, Akt phosphorylation increased markedly by the treatment of humanized 3H7 antibodies. These data indicate that the humanized anti-Tie2 antibodies are able to strongly induce the activation of Akt, the main downstream signaling molecule of Tie2 receptor in endothelial cells.

Example 7

The Effect of 3H7H12G4 in a Mouse Model of Primary Open-Angle Glaucoma

Figure 8E:
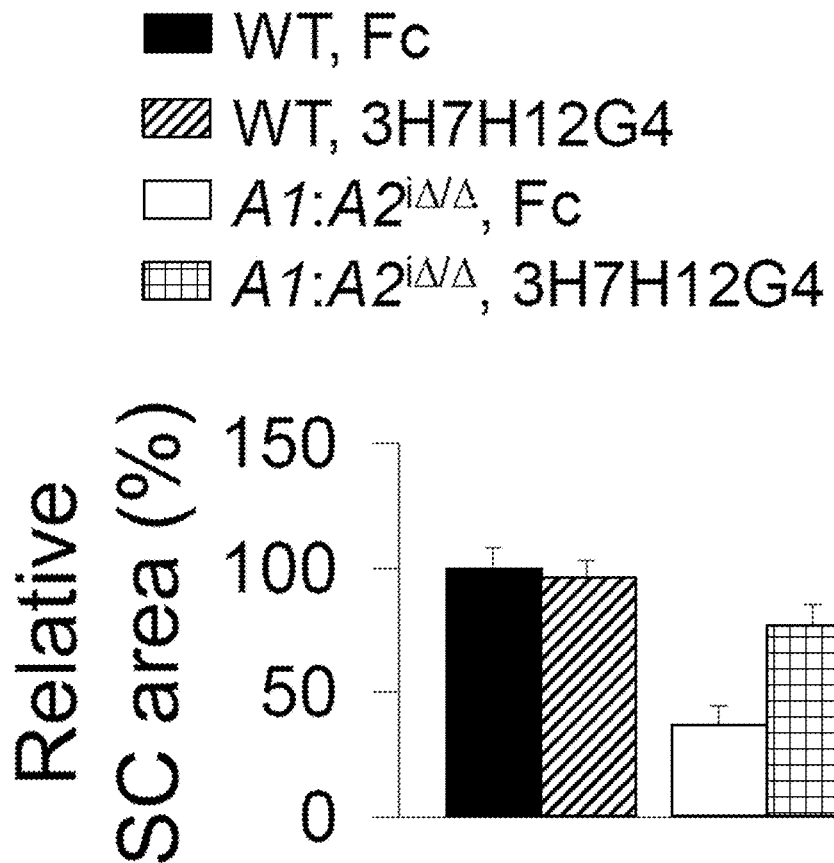
Figure 8F:
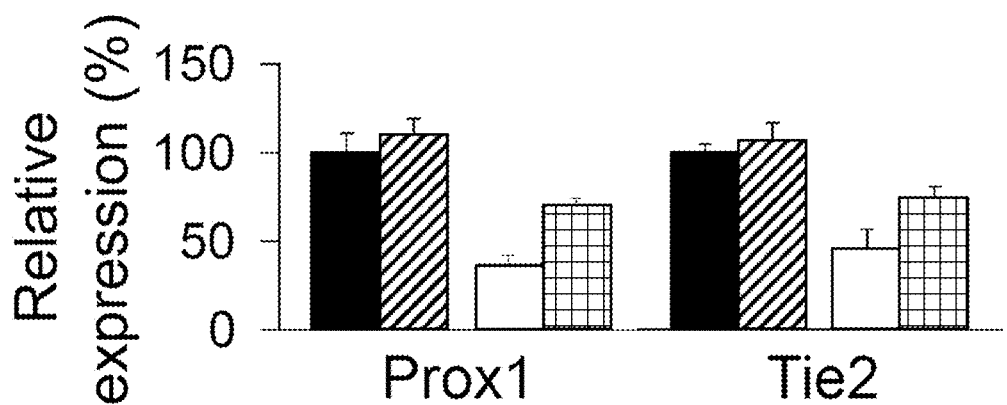

To test whether Tie2 activation by 3H7H12G4 could rescue regressed SC (Schlemm's canal) and lower IOP (intraocular pressure), we used a mouse model of primary open-angle glaucoma. The model is made by tamoxifen administration into 8-weeks-old double Angiopoietin-1/Angiopoietin-2 deficient (A1:A2$^{i\Delta/\Delta}$) mice for inducible deletion of both angiopoietin-1 and -2 genes (FIG. 8A). The intraocular administration of 3H7H12G4 (~5 µg, one eye) and Fc (~5 µg, contralateral eye) was performed at 12 weeks old (FIG. 8A). To intravitreally administer indicated reagents, ~1 µl (5 mg/ml) containing 5 µg of each reagent was injected into the vitreal cavity using the Nanoliter 2000 micro-injector (World Precision Instruments) fitted with a glass capillary pipette. IOP measurements were performed with a rebound tonometer (TonoLab) at 12, 13 and 14 weeks old (FIG. 8A). IOP was measured by placing the tip of the pressure sensor approximately ⅛ inch from the central cornea immediately after anesthetizing the mice. The digital readouts of 5 consecutive IOP measurements were acquired from the tonometer. In wild-type mice, there is no difference of IOP between 3H7H12G4-treated eyes and Fc-treated eyes (FIG. 8C). On the other hand, A1:A2$^{i\Delta/\Delta}$ mice showed significant decrease of IOP in 3H7H12G4-treated eyes by 25.6% compared with that of Fc-treated eyes (FIG. 8D). CD144$^+$ SC area and intensities of Prox1 and Tie2 immunostaining in CD144$^+$ SC were measured at 2 weeks after 3H7H12G4 administration. Anti-CD144 antibody (1:200, BD Biosciences), anti-Prox1 antibody (1:200, ReliaTech), and anti-Tie2 antibody (1:200, R&D systems) were used. CD144$^+$ SC area of whole-mounted cornea was calculated as a percentage of the CD144$^+$ area divided by its control area. A1:A2$^{i\Delta/\Delta}$ mice showed significant increase of SC area in 3H7H12G4-treated eyes by 114.8% compared with that of Fc-treated eyes (FIGS. 8B, E). To quantify the relative expression of Prox1, intensities were measured in the nucleus region of CD144$^+$ SC. A1:A2$^{i\Delta/\Delta}$ mice showed significant increase of Prox1 intensity in 3H7H12G4-treated eyes by 88.4% compared with that of Fc-treated eyes (FIGS. 8B, F). To quantify the expression of Tie2, intensities were measured in the CD144$^+$ SC area. A1:A2$^{i\Delta/\Delta}$ mice showed significant increase of Tie2 intensity in 3H7H12G4-treated eyes by 63.0% compared with that of Fc-treated eyes (FIGS. 8B, F). Overall, these findings indicate that Tie2 activation by 3H7H12G4 rescues the impaired SC of A1:A2$^{i\Delta/\Delta}$ mice.

Example 8

Figure 9A:
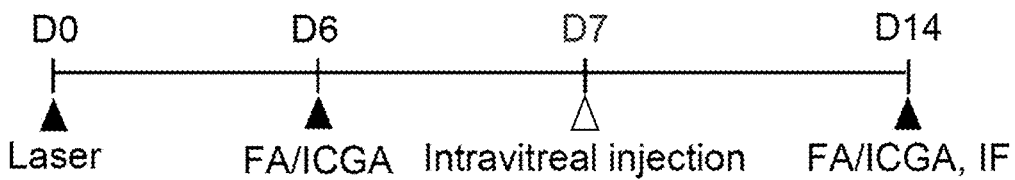
FIGS. 9A-9C shows suppression of CNV (Choroidal Neo-Vascularization) and vascular leakage by intravitreally injected 3H7H12G4 in laser-induced CNV model. The intravitreal administration of antibodies (1 µl injection of 5 mg/ml solution) was performed at 7 days after laser photocoagulation. CD31$^+$ CNV volumes were measured and leaky areas around CNV were calculated as the total measured hyper-fluorescent areas in FA images divided by the total measured CNV areas in ICGA images at 6 and/or 14 days after laser photocoagulation. n=11 for each group. Values are mean±SD. *p<0.05, ***p<0.001 by one-way ANOVA followed by Student-Newman-Keuls post-test; ##p<0.01, ###p<0.001 by paired Student's t-test.
Figure 9B:
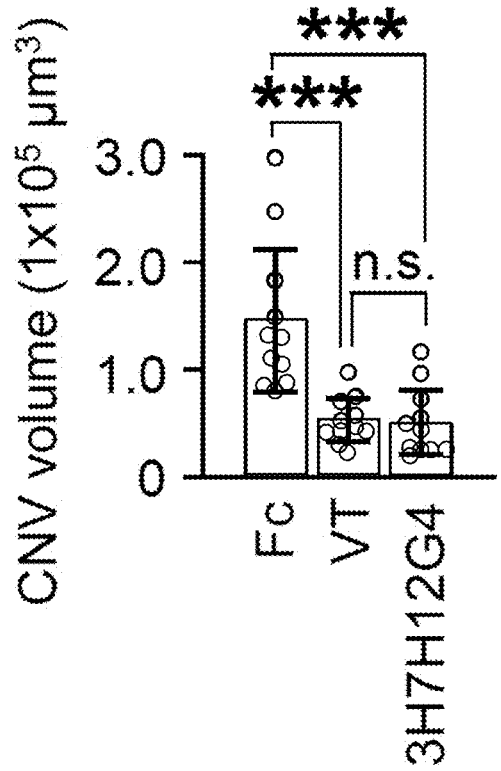
Figure 9C:
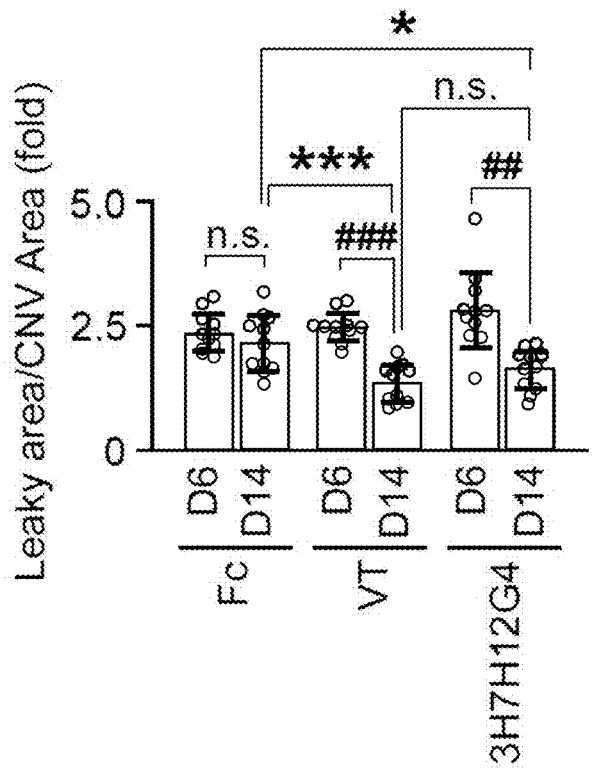

CNV Regression and Vascular Leakage Suppression by Intravitreally Injected 3H7H12G4 in Laser-Induced CNV Model 3H7H12G4 was tested for its ability to inhibit choroidal neovascularization (CNV), the hallmark of wet age-related macular degeneration (AMD) using laser-induced CNV model. After dilation of pupils with 5 mg/ml phenylephrine and 5 mg/ml tropicamide eye drops (Santen Pharmaceutical) and instillation of 0.5% proparacaine hydrochloride eye drops (Alcon) for topical anesthesia, laser photocoagulator (Lumenis Inc.) with a slit lamp delivery system was used with a glass coverslip as a contact lens to visualize the retina. Sufficient laser energy (532 nm wavelength, 250 mW power, 100 ms duration, 50 µm spot size) was delivered in 4 locations for each eye (the 3, 6, 9 and 12 o'clock positions of the posterior pole). Only burns that produced a bubble at the time of laser photocoagulation, indicating the rupture of the Bruch's membrane, were included in this study. Spots containing hemorrhage at the laser site were excluded from the analysis. To recapitulate a clinical situation, 3H7H12G4 (5 µg) was administered intravitreally to the mice at 7 days after laser photocoagulation (FIG. 9A). As a control or as for comparison, Fc or VEGF-Trap (5 µg each) was administered in a same manner to the mice. To intravitreally administer indicated reagents, ~1 µl (5 mg/ml) containing 5 µg of each reagent was injected into the vitreal cavity using the Nanoliter 2000 micro-injector (World Precision Instruments) fitted with a glass capillary pipette. CD31$^+$ CNV volumes of the retinal pigment epithelium (RPE)—choroid—sclera flat mounts were calculated using the MATLAB image processing toolbox (MathWorks) at 14 days after laser photocoagulation. Anti-CD31 antibody (1:200, Millipore) was used for the detection of endothelial cells of CNV. VEGF-Trap effectively induced CNV regression by 64.4% compared with Fc, and 3H7H12G4 similarly induced CNV regression (65.7%) (FIG. 9B). Combined fluorescein angiography (FA) and indocyanine green angiography (ICGA) enabled us to measure vascular leakage at the neovessels around the laser injury site. Continuous-wave laser modules at 488 nm and 785 nm were used as excitation sources for fluorescein and ICG, respectively. A raster scanning pattern of excitation lasers was achieved by a scanner system consisting of a rotating polygonal mirror (MC-5; Lincoln Laser) and a galvanometer-based scanning mirror (6230H; Cambridge technology), and delivered to the back aperture of an imaging lens. A high numerical aperture (NA) objective lens (PlanApo λ, NA 0.75; Nikon) was used as the imaging lens to provide wide-field fundus fluorescence images. Fluorescence signals detected by photomultiplier tubes (R9110; Hamamatsu Photonics) were digitized by frame grabber and reconstructed to images with size of 512×512 pixels per frame in real time. To visualize late-phase (6 min) FA and ICGA images utilizing the angiography system, 10 mg of fluorescein sodium (Alcon) and 0.15 mg of ICG (Daiichi Pharmaceutical) were administered intraperitoneally and intravenously, respectively. The imaging procedure was performed under systemic anesthesia and pupil dilation to improve the quality of images. Leaky areas from CNV were calculated as the total measured hyperfluorescent areas in FA images divided by the total measured CNV areas in ICGA images using a Java-based imaging software (ImajeJ; National Institutes of Health). Compared with Fc, both VEGF-Trap (37.0%) and 3H7H12G4 (24.6%) similarly suppressed vascular leakage (FIG. 9C). Of note, the Fc-treated group showed no significant difference in vascular leakage between 6 and 14 days after laser photocoagulation, but VEGF-Trap and 3H7H12G4 markedly reduced vascular leakage (45.6% and 42.5%, respectively) (FIG. 9C). Thus, the magnitude of the suppression of CNV and vascular leakage was quantitatively indistinguishable between VEGF-Trap and 3H7H12G4 in the mouse model of laser-induced CNV.

Example 9

Co-Localization of 3H7H12G4 and CD31 in Endothelial Cells of CNV

To investigate whether subcutaneously injected 3H7H12G4 can also exert the therapeutic effects on CNV, we firstly evaluated co-localization of 3H7H12G4 and CD31 in endothelial cells of CNV. The subcutaneous administration of 3H7H12G4 (25 mg/kg) was performed at 1 day after laser photocoagulation. As a control, Fc (25 mg/kg) was administered in a same manner to the mice. The co-localization of 3H7H12G4 and anti-CD31 antibody (1:200, Millipore) in endothelial cells of CNV was directly detected by anti-human IgG antibody (1:1000, Jackson ImmunoResearch Laboratories) at 2, 4, and 8 days after laser photocoagulation (FIG. 10A). The administered 3H7H12G4 was highly detectable in the CD31$^+$ endothelial cells CNV (FIG. 10B-D).

Example 10

The CNV Inhibition Effect of Subcutaneously Injected 3H7H12G4 Antibody

To determine the effect of subcutaneously injected 3H7H12G4 in CNV inhibition, the subcutaneous administration of 3H7H12G4 (25 mg/kg) was performed at 1 day after laser photocoagulation. As a control, Fc (25 mg/kg) was administered in a same manner to the mice. Anti-CD31 antibody (1:200, Millipore) was used for the detection of endothelial cells of CNV, and CD31$^+$ CNV volumes of the RPE—choroid—sclera flat mounts were calculated using the MATLAB image processing toolbox (MathWorks) at 8 days after laser photocoagulation (FIG. 11A). 3H7H12G4 effectively inhibited CNV formation by 69.9% compared with Fc (FIGS. 11B, C), indicating that not only intravitreal injection but also subcutaneous injection of 3H7H12G4 have the inhibitory effect on CNV.

INDUSTRIAL APPLICABILITY

The antibody or antigen-binding fragment thereof that binds to Tie2 according to the present invention is binding to Tie2 with a high affinity, maintains cross-reactivity to humans and mice, and shows the desired antigen reactivity. In addition, by inducing the Tie2 phosphorylation and the activation of the Tie2 receptor, it can be usefully used to prevent or treat angiogenic diseases of interest.

Until now, specific parts of the content in the present invention has been described in detail, and it will be obvious to those having ordinary knowledge in the art that these specific technologies are merely preferable embodiments and thus the scope of the present invention is not limited to the embodiments.

SEQUENCE LIST FREE TEXT

The electric file attached.

The invention claimed is:

1. An anti-Tie2 antibody or antigen-binding fragment thereof which binds Tie2 Ig3-FNIII (1-3) domain comprising the sequence of SEQ ID NO:2, wherein the antibody or antigen-binding fragment thereof comprises:
a heavy chain variable region comprising heavy chain CDRH1, CDRH2, and CDRH3 comprising amino acid sequences of SEQ ID NOs:3-5, respectively, and a light chain variable region comprising light chain CDRL1, CDRL2, and CDRL3 comprising amino acid sequences of SEQ ID NOs:6-8, respectively;
a heavy chain variable region comprising heavy chain CDRH1, CDRH2, and CDRH3 comprising amino acid sequences of SEQ ID NOs:13-15, respectively, and a light chain variable region comprising light chain CDRL1, CDRL2, and CDRL3 comprising amino acid sequences of SEQ ID NOs:16-18, respectively;

a heavy chain variable region comprising heavy chain CDRH1, CDRH2, and CDRH3 comprising amino acid sequences of SEQ ID NOs:23-25, respectively, and a light chain variable region comprising light chain CDRL1, CDRL2, and CDRL3 comprising amino acid sequences of SEQ ID NOs:26-28, respectively;

a heavy chain variable region comprising heavy chain CDRH1, CDRH2, and CDRH3 comprising amino acid sequences of SEQ ID NOs:33-35, respectively, and a light chain variable region comprising light chain CDRL1, CDRL2, and CDRL3 comprising amino acid sequences of SEQ ID NOs:36-38, respectively; or a heavy chain variable region comprising heavy chain CDRH1, CDRH2, and CDRH3 comprising amino acid sequences of SEQ ID NOs:43-45, respectively, and a light chain variable region comprising light chain CDRL1, CDRL2, and CDRL3 comprising amino acid sequences of SEQ ID NO:46-48, respectively.

2. The antibody or antigen-binding fragment thereof of claim 1, wherein the antibody or antigen-binding fragment thereof comprises:

a heavy chain variable region comprising amino acid sequence of SEQ ID NO:9 and a light chain variable region comprising amino acid sequence of SEQ ID NO:11;

a heavy chain variable region comprising amino acid sequence of SEQ ID NO:19 and a light chain variable region comprising amino acid sequence of SEQ ID NO:21;

a heavy chain variable region comprising amino acid sequence of SEQ ID NO:29 and a light chain variable region comprising amino acid sequence of SEQ ID NO:31;

a heavy chain variable region comprising amino acid sequence of SEQ ID NO:39 and a light chain variable region comprising amino acid sequence of SEQ ID NO:41;

a heavy chain variable region comprising amino acid sequence of SEQ ID NO:49 and a light chain variable region comprising amino acid sequence of SEQ ID NO:51;

a heavy chain variable region comprising amino acid sequence of SEQ ID NO:53 and a light chain variable region comprising amino acid sequence of SEQ ID NO:54;

a heavy chain variable region comprising amino acid sequence of SEQ ID NO:57 and a light chain variable region comprising amino acid sequence of SEQ ID NO:58;

a heavy chain variable region comprising amino acid sequence of SEQ ID NO:61 and a light chain variable region comprising amino acid sequence of SEQ ID NO:62; or a heavy chain variable region comprising amino acid sequence of SEQ ID NO:65 and a light chain variable region comprising amino acid sequence of SEQ ID NO:66.

3. The antibody or antigen-binding fragment thereof of claim 1, wherein the antibody or antigen-binding fragment thereof comprises a heavy chain variable region comprising a heavy chain CDRs comprising amino acid sequences of SEQ ID NOs:23-25 and a light chain variable region comprising a light chain CDRs comprising amino acid sequences of SEQ ID NOs:26-28.

4. The antibody or antigen-binding fragment thereof of claim 1, wherein the antibody or antigen-binding fragment thereof comprises a heavy chain variable region comprising amino acid sequence of SEQ ID NO:29 and a light chain variable region comprising amino acid sequence of SEQ ID NO:31.

5. A pharmaceutical composition comprising the antibody or antigen-binding fragment thereof of claim 1 and a pharmaceutically acceptable excipient.

6. A pharmaceutical composition comprising the antibody or antigen-binding fragment thereof of claim 3 and a pharmaceutically acceptable excipient.

* * * * *

```
                        SEQUENCE LISTING

<160> NUMBER OF SEQ ID NOS: 68

<210> SEQ ID NO 1
<211> LENGTH: 1124
<212> TYPE: PRT
<213> ORGANISM: Artificial Sequence
<220> FEATURE:
<223> OTHER INFORMATION: Synthetic Sequence

<400> SEQUENCE: 1

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160
```

```
Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Gln Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
    370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
    450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575
```

```
Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
        595                 600                 605

Glu Gln Tyr Val Val Arg Ala Arg Val Asn Thr Lys Ala Gln Gly Glu
    610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
        675                 680                 685

Ile Lys Asn Ala Thr Ile Thr Gln Tyr Gln Leu Lys Gly Leu Glu Pro
    690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Met Leu Leu Ile Ala Ile Leu
            740                 745                 750

Gly Ser Ala Gly Met Thr Cys Leu Thr Val Leu Leu Ala Phe Leu Ile
        755                 760                 765

Ile Leu Gln Leu Lys Arg Ala Asn Val Gln Arg Arg Met Ala Gln Ala
    770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
                805                 810                 815

Pro Val Leu Asp Trp Asn Asp Ile Lys Phe Gln Asp Val Ile Gly Glu
            820                 825                 830

Gly Asn Phe Gly Gln Val Leu Lys Ala Arg Ile Lys Lys Asp Gly Leu
        835                 840                 845

Arg Met Asp Ala Ala Ile Lys Arg Met Lys Glu Tyr Ala Ser Lys Asp
    850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                885                 890                 895

Tyr Leu Tyr Leu Ala Ile Glu Tyr Ala Pro His Gly Asn Leu Leu Asp
            900                 905                 910

Phe Leu Arg Lys Ser Arg Val Leu Glu Thr Asp Pro Ala Phe Ala Ile
        915                 920                 925

Ala Asn Ser Thr Ala Ser Thr Leu Ser Ser Gln Leu Leu His Phe
    930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
                965                 970                 975

Val Ala Lys Ile Ala Asp Phe Gly Leu Ser Arg Gly Gln Glu Val Tyr
            980                 985                 990

Val Lys Lys Thr Met Gly Arg Leu  Pro Val Arg Trp Met  Ala Ile Glu
```

```
                995                1000               1005
Ser Leu Asn Tyr Ser Val Tyr Thr Thr Asn Ser Asp Val Trp Ser
    1010               1015               1020

Tyr Gly Val Leu Leu Trp Glu Ile Val Ser Leu Gly Gly Thr Pro
    1025               1030               1035

Tyr Cys Gly Met Thr Cys Ala Glu Leu Tyr Glu Lys Leu Pro Gln
    1040               1045               1050

Gly Tyr Arg Leu Glu Lys Pro Leu Asn Cys Asp Asp Glu Val Tyr
    1055               1060               1065

Asp Leu Met Arg Gln Cys Trp Arg Glu Lys Pro Tyr Glu Arg Pro
    1070               1075               1080

Ser Phe Ala Gln Ile Leu Val Ser Leu Asn Arg Met Leu Glu Glu
    1085               1090               1095

Arg Lys Thr Tyr Val Asn Thr Thr Leu Tyr Glu Lys Phe Thr Tyr
    1100               1105               1110

Ala Gly Ile Asp Cys Ser Ala Glu Glu Ala Ala
    1115               1120

<210> SEQ ID NO 2
<211> LENGTH: 390
<212> TYPE: PRT
<213> ORGANISM: Artificial Sequence
<220> FEATURE:
<223> OTHER INFORMATION: Synthetic Sequence

<400> SEQUENCE: 2

Thr Pro Lys Ile Val Asp Leu Pro Asp His Ile Glu Val Asn Ser Gly
1               5                   10                  15

Lys Phe Asn Pro Ile Cys Lys Ala Ser Gly Trp Pro Leu Pro Thr Asn
            20                  25                  30

Glu Glu Met Thr Leu Val Lys Pro Asp Gly Thr Val Leu His Pro Lys
        35                  40                  45

Asp Phe Asn His Thr Asp His Phe Ser Val Ala Ile Phe Thr Ile His
    50                  55                  60

Arg Ile Leu Pro Pro Asp Ser Gly Val Trp Val Cys Ser Val Asn Thr
65                  70                  75                  80

Val Ala Gly Met Val Glu Lys Pro Phe Asn Ile Ser Val Lys Val Leu
                85                  90                  95

Pro Lys Pro Leu Asn Ala Pro Asn Val Ile Asp Thr Gly His Asn Phe
            100                 105                 110

Ala Val Ile Asn Ile Ser Ser Glu Pro Tyr Phe Gly Asp Gly Pro Ile
        115                 120                 125

Lys Ser Lys Lys Leu Leu Tyr Lys Pro Val Asn His Tyr Glu Ala Trp
    130                 135                 140

Gln His Ile Gln Val Thr Asn Glu Ile Val Thr Leu Asn Tyr Leu Glu
145                 150                 155                 160

Pro Arg Thr Glu Tyr Glu Leu Cys Val Gln Leu Val Arg Arg Gly Glu
                165                 170                 175

Gly Gly Glu Gly His Pro Gly Pro Val Arg Arg Phe Thr Thr Ala Ser
            180                 185                 190

Ile Gly Leu Pro Pro Arg Gly Leu Asn Leu Leu Pro Lys Ser Gln
        195                 200                 205

Thr Thr Leu Asn Leu Thr Trp Gln Pro Ile Phe Pro Ser Ser Glu Asp
    210                 215                 220

Asp Phe Tyr Val Glu Val Glu Arg Arg Ser Val Gln Lys Ser Asp Gln
```

```
                225                 230                 235                 240
        Gln Asn Ile Lys Val Pro Gly Asn Leu Thr Ser Val Leu Leu Asn Asn
                        245                 250                 255
        Leu His Pro Arg Glu Gln Tyr Val Val Arg Ala Arg Val Asn Thr Lys
                        260                 265                 270
        Ala Gln Gly Glu Trp Ser Glu Asp Leu Thr Ala Trp Thr Leu Ser Asp
                        275                 280                 285
        Ile Leu Pro Pro Gln Pro Glu Asn Ile Lys Ile Ser Asn Ile Thr His
                        290                 295                 300
        Ser Ser Ala Val Ile Ser Trp Thr Ile Leu Asp Gly Tyr Ser Ile Ser
        305                 310                 315                 320
        Ser Ile Thr Ile Arg Tyr Lys Val Gln Gly Lys Asn Glu Asp Gln His
                        325                 330                 335
        Val Asp Val Lys Ile Lys Asn Ala Thr Ile Thr Gln Tyr Gln Leu Lys
                        340                 345                 350
        Gly Leu Glu Pro Glu Thr Ala Tyr Gln Val Asp Ile Phe Ala Glu Asn
                        355                 360                 365
        Asn Ile Gly Ser Ser Asn Pro Ala Phe Ser His Glu Leu Val Thr Leu
                        370                 375                 380
        Pro Glu Ser Gln Ala Pro
        385                 390

<210> SEQ ID NO 3
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 3

Ser Tyr Trp Met Asn
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 4

Met Ile His Pro Ser Asp Ser Glu Thr Arg Leu Asn Gln Lys Phe Lys
1               5                   10                  15

Asp

<210> SEQ ID NO 5
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 5

Gly Asn Tyr Phe Asp Cys
1               5

<210> SEQ ID NO 6
<211> LENGTH: 11
<212> TYPE: PRT
<213> ORGANISM: Artificial Sequence
<220> FEATURE:
```

<223> OTHER INFORMATION: Synthetic Sequence

<400> SEQUENCE: 6

Arg Ala Ser Gln Asp Ile Gly Ile Ser Leu Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 7

Ala Thr Ser Ile Leu Asp Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 8

Leu Gln Tyr Ala Ser Ser Pro Trp Thr
1               5

<210> SEQ ID NO 9
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 9

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Ser Tyr
                20                  25                  30

Trp Met Asn Trp Val Lys Gln Arg Pro Gly Gln Gly Leu Glu Trp Ile
            35                  40                  45

Gly Met Ile His Pro Ser Asp Ser Glu Thr Arg Leu Asn Gln Lys Phe
        50                  55                  60

Lys Asp Lys Ala Thr Leu Thr Val Asp Lys Ser Ser Ser Thr Ala Tyr
65                  70                  75                  80

Leu Gln Leu Ser Ser Pro Thr Ser Glu Asp Ser Ala Val Tyr Tyr Cys
                85                  90                  95

Ala Arg Gly Asn Tyr Phe Asp Cys Trp Gly Gln Gly Thr Thr Leu Thr
            100                 105                 110

Val Ser Ser
        115

<210> SEQ ID NO 10
<211> LENGTH: 345
<212> TYPE: DNA
<213> ORGANISM: Artificial Sequence
<220> FEATURE:
<223> OTHER INFORMATION: Synthetic Sequence

<400> SEQUENCE: 10
caggtccaac tgcagcagcc tggggctgag ctggtgaggc ctggagcttc agtgaagctg    60

```
tcctgcaagg cttctggcta ctccttcacc agctactgga tgaactgggt gaagcagagg    120
cctggacaag gccttgagtg gattggcatg attcatcctt ccgatagtga aactaggtta    180
aatcagaagt tcaaggacaa ggccacattg actgtagaca atcctccag cacagcctac    240 ttgcaactca gcagcccgac atctgaggac tctgcggtct attactgtgc aaggggaac    300 tactttgact gctggggcca aggcaccact ctcacagtct cctca                   345
```

<210> SEQ ID NO 11
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 11

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ile Ser
            20                  25                  30

Leu Asn Trp Leu Gln Gln Glu Pro Asp Gly Thr Ile Lys Arg Leu Ile
        35                  40                  45

Tyr Ala Thr Ser Ile Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Trp
                85                  90                  95

Thr Phe Gly Gly Gly Thr Lys Leu Glu Ile Lys
            100                 105
```

<210> SEQ ID NO 12
<211> LENGTH: 321
<212> TYPE: DNA
<213> ORGANISM: Artificial Sequence
<220> FEATURE:
<223> OTHER INFORMATION: Synthetic Sequence

<400> SEQUENCE: 12

```
gacatccaga tgacccagtc tccatcctcc ttatctgcct ctctgggaga aagggtcagt    60
ctcacttgtc gggcaagtca ggacattggt attagcttaa actggcttca gcaggaacca    120
gatggaacta ttaaacgcct gatctacgcc acatccattt tagattctgg tgtccccaaa    180
aggttcagtg gcagtaggtc tgggtcagat tattctctca ccatcagcag ccttgagtct    240
gaagattttg tagactatta ctgtctacaa tatgctagtt ctccgtggac gttcggtgga    300
ggcaccaagc tggaaatcaa a                                              321
```

<210> SEQ ID NO 13
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 13

```
Ser Tyr Trp Met Asn
1               5
```

<210> SEQ ID NO 14
<211> LENGTH: 17

```
<212> TYPE: PRT
<213> ORGANISM: Artificial Sequence
<220> FEATURE:
<223> OTHER INFORMATION: Synthetic Sequence

<400> SEQUENCE: 14

Met Ile His Pro Ser Asp Ser Glu Thr Arg Leu Asn Gln Lys Phe Lys
1               5                   10                  15

Asp

<210> SEQ ID NO 15
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 15

Gly Tyr Tyr Phe Gly Tyr
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 16

Arg Ala Ser Gln Asp Ile Gly Ile Ser Leu Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 17

Ala Thr Ser Asn Leu Asp Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 18

Leu Gln Tyr Ala Ser Ser Pro Pro Thr
1               5

<210> SEQ ID NO 19
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 19

Gln Val Gln Leu Gln Gln Pro Gly Ala Asp Leu Val Arg Pro Gly Ala
1               5                   10                  15

Ser Val Lys Leu Ser Cys Lys Ala Ser Gly Tyr Ser Phe Thr Ser Tyr
                20                  25                  30
```

```
Trp Met Asn Trp Val Lys Gln Arg Pro Gly Gln Gly Leu Glu Trp Ile
        35                  40                  45

Gly Met Ile His Pro Ser Asp Ser Glu Thr Arg Leu Asn Gln Lys Phe
 50                  55                  60

Lys Asp Lys Ala Thr Leu Thr Val Asp Lys Ser Ser Thr Ala Tyr
 65                  70                  75                  80

Met Gln Leu Ser Ser Pro Thr Ser Glu Asp Ser Ala Val Tyr Tyr Cys
                 85                  90                  95

Ala Lys Gly Tyr Tyr Phe Gly Tyr Trp Gly Gln Gly Thr Thr Leu Thr
                100                 105                 110

Val Ser Ser
        115
```

<210> SEQ ID NO 20
<211> LENGTH: 345
<212> TYPE: DNA
<213> ORGANISM: Artificial Sequence
<220> FEATURE:
<223> OTHER INFORMATION: Synthetic Sequence

<400> SEQUENCE: 20

```
caggtccaac tgcagcagcc tggggctgac ctggtgaggc ctggagcttc agtgaagctg    60
tcctgcaagg cttctggcta ctccttcacc agctactgga tgaactgggt gaagcagagg   120
cctggacaag gccttgagtg gattggcatg attcatcctt ccgatagtga aactaggtta   180
aatcagaagt tcaaggacaa ggccacattg actgtagaca atcctccag cacagcctac    240
atgcaactca gcagcccgac atctgaggac tctgcggtct attactgtgc aaaggggtac   300
tactttggct actggggcca aggcaccact ctcacagtct cctca                   345
```

<210> SEQ ID NO 21
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 21

```
Asp Ile Gln Met Thr Gln Ser Pro Ser Ser Leu Ser Ala Ser Leu Gly
 1               5                  10                  15

Glu Arg Val Ser Leu Thr Cys Arg Ala Ser Gln Asp Ile Gly Ile Ser
                20                  25                  30

Leu Asn Trp Leu Gln Gln Glu Pro Asp Gly Thr Ile Lys Arg Leu Ile
        35                  40                  45

Tyr Ala Thr Ser Asn Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
 65                  70                  75                  80

Glu Asp Phe Val Asp Tyr Tyr Cys Leu Gln Tyr Ala Ser Ser Pro Pro
                 85                  90                  95

Thr Phe Gly Gly Gly Thr Lys Leu Glu Ile Lys
                100                 105
```

<210> SEQ ID NO 22
<211> LENGTH: 321
<212> TYPE: DNA
<213> ORGANISM: Artificial Sequence
<220> FEATURE:
<223> OTHER INFORMATION: Synthetic Sequence

<400> SEQUENCE: 22

```
gacatccaga tgacccagtc tccatcctcc ttatctgcct ctctgggaga aagagtcagt      60
ctcacttgtc gggcaagtca ggacattggt attagtttaa actggcttca gcaggaacca     120
gatggaacta ttaaacgcct gatctacgcc acatccaatt tagattctgg tgtccccaaa     180
aggttcagtg gcagtaggtc tgggtcagat tattctctca ccatcagcag ccttgagtct     240
gaagattttg tagactatta ctgtctacaa tatgctagtt ctcctccgac gttcggtgga     300
ggcaccaagc tggaaatcaa a                                                321
```

<210> SEQ ID NO 23
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 23

```
Ser Tyr Trp Met Asn
1               5
```

<210> SEQ ID NO 24
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 24

```
Met Ile His Pro Ser Asp Ser Glu Thr Arg Leu Asn Gln Lys Phe Met
1               5                   10                  15

Asp
```

<210> SEQ ID NO 25
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 25

```
Gly Leu Tyr Gly Asn Ser
1               5
```

<210> SEQ ID NO 26
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 26

```
Arg Ala Ser Gln Asp Ile Gly Ile Ser Leu Asn
1               5                   10
```

<210> SEQ ID NO 27
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 27

Ala Thr Ser Ser Leu Asp Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 28

Leu Gln Tyr Ala Ser Ser Pro Tyr Thr
1               5

<210> SEQ ID NO 29
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 29

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Ser Tyr
                20                  25                  30

Trp Met Asn Trp Val Lys Gln Arg Pro Gly Gln Gly Leu Glu Trp Ile
            35                  40                  45

Gly Met Ile His Pro Ser Asp Ser Glu Thr Arg Leu Asn Gln Lys Phe
        50                  55                  60

Met Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Gly Leu Tyr Gly Asn Ser Trp Gly Gln Gly Thr Leu Val Thr
                100                 105                 110

Val Ser Ala
        115

<210> SEQ ID NO 30
<211> LENGTH: 345
<212> TYPE: DNA
<213> ORGANISM: Artificial Sequence
<220> FEATURE:
<223> OTHER INFORMATION: Synthetic Sequence

<400> SEQUENCE: 30
caggtccaac tgcagcagcc tggggctgag ctggtgaggc ctggagcttc agtgaagctg     60
tcctgcaagg cttctggcta ctccttcacc agctactgga tgaactgggt gaagcagagg    120
cctggacaag gccttgagtg gattggcatg attcatcctt ccgatagtga aactaggtta    180
aatcagaagt tcatggacaa ggccacattg actgtagaca atcctccag cacagcctac     240 atgcagctca gcagcccgac atctgaggac tctgcggtct attactgtgc tcgtggcctc    300
tatggtaact cttggggcca agggactctg gtcactgtct ctgca                    345

<210> SEQ ID NO 31
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 31

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ile Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Tyr
                85                  90                  95

Thr Phe Gly Gly Gly Thr Lys Leu Glu Ile Lys
            100                 105

<210> SEQ ID NO 32
<211> LENGTH: 321
<212> TYPE: DNA
<213> ORGANISM: Artificial Sequence
<220> FEATURE:
<223> OTHER INFORMATION: Synthetic Sequence

<400> SEQUENCE: 32
gacatccaga tgacccagtc tccatcctcc ttatctgcct ctctgggaga aagagtcagt    60
ctcacttgtc gggcaagtca ggacattggt attagcttaa actggcttca gcaggaacca   120
gatggaacta ttaaacgcct gatctacgcc acatccagtt tagattctgg tgtccccaaa   180
aggttcagtg gcagtaggtc tgggtcagat tattctctca ccatcagcag ccttgagtct   240
gaagattttg tagactatta ctgtctacaa tatgctagtt ctccgtacac gttcggaggg   300
gggaccaagc tggaaataaa a                                             321

<210> SEQ ID NO 33
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 33

Ser Tyr Trp Met Asn
1               5

<210> SEQ ID NO 34
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 34

Met Ile His Pro Ser Asp Ser Glu Thr Arg Leu Asn Gln Lys Phe Lys
1               5                   10                  15

Asp

<210> SEQ ID NO 35
<211> LENGTH: 6
<212> TYPE: PRT
<213> ORGANISM: Artificial Sequence

```
<220> FEATURE:
<223> OTHER INFORMATION: Synthetic Sequence

<400> SEQUENCE: 35

Gly Tyr Tyr Phe Asp Tyr
1               5

<210> SEQ ID NO 36
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 36

Arg Ala Ser Gln Asp Ile Gly Ile Ser Leu Asn
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 37

Ala Thr Ser Ser Leu Asp Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 38

Leu Gln Tyr Val Ser Ser Pro Trp Thr
1               5

<210> SEQ ID NO 39
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 39

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Gly Tyr Tyr Phe Asp Tyr Trp Gly Gln Gly Thr Thr Leu Thr
            100                 105                 110

Val Ser Ser
```

<210> SEQ ID NO 40
<211> LENGTH: 345
<212> TYPE: DNA
<213> ORGANISM: Artificial Sequence
<220> FEATURE:
<223> OTHER INFORMATION: Synthetic Sequence

<400> SEQUENCE: 40

```
caggtccaac tgcagcagcc tggggctgag ctggtgaggc tggagcttc   agtgaagctg     60
tcctgcaagg cttctggcta ctccttcacc agctactgga tgaactgggt gaagcagagg    120
cctggacaag gccttgagtg gattggcatg attcatcctt ccgatagtga aactaggtta    180
aatcagaagt tcaaggacaa ggccacattg actgtagaca atcctccag  cacagcctac    240
atgcaactca gcagcccgac atctgaggac tctgcggtct attactgtgc aagaggctac    300
tactttgact actggggcca aggcaccact ctcacagtct cctca                    345
```

<210> SEQ ID NO 41
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 41

```
Asp Ile Gln Met Thr Gln Ser Pro Ser Ser Leu Ser Ala Ser Leu Gly
1               5                   10                  15
Glu Arg Val Ser Leu Thr Cys Arg Ala Ser Gln Asp Ile Gly Ile Ser
            20                  25                  30
Leu Asn Trp Leu Gln Gln Glu Pro Asp Gly Thr Ile Lys Arg Leu Ile
        35                  40                  45
Tyr Ala Thr Ser Ser Leu Asp Ser Gly Val Pro Lys Arg Phe Thr Gly
    50                  55                  60
Ser Arg Ser Gly Ser Asp Tyr Ser Leu Thr Ile Ser Ser Leu Glu Ser
65                  70                  75                  80
Glu Asp Phe Val Asp Tyr Tyr Cys Leu Gln Tyr Val Ser Ser Pro Trp
                85                  90                  95
Thr Phe Gly Gly Gly Thr Lys Leu Glu Ile Lys
            100                 105
```

<210> SEQ ID NO 42
<211> LENGTH: 321
<212> TYPE: DNA
<213> ORGANISM: Artificial Sequence
<220> FEATURE:
<223> OTHER INFORMATION: Synthetic Sequence

<400> SEQUENCE: 42

```
gacatccaga tgacccagtc tccatcctcc ttatctgcct ctctgggaga aagagtcagt     60
ctcacttgtc gggcaagtca ggacattggt attagcttaa actggcttca gcaggaacca    120
gatggaacta ttaaacgcct gatctacgcc acatccagtt tagattctgg tgtcccaag    180
aggttcactg gcagtaggtc tggtgtcagat tattctctca ccatcagcag ccttgagtct    240
gaagattttg tagactatta ctgtctacaa tatgttagtt ctccgtggac gttcggtgga    300
ggcaccaagc tggaaatcaa a                                              321
```

<210> SEQ ID NO 43

```
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 43

Ser Tyr Trp Met Asn
1               5

<210> SEQ ID NO 44
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 44

Met Ile His Pro Ser Asp Ser Glu Thr Arg Leu Asn Gln Lys Phe Lys
1               5                   10                  15

Asp

<210> SEQ ID NO 45
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 45

Leu Thr Ile Tyr Phe Asp Tyr
1               5

<210> SEQ ID NO 46
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 46

Arg Ala Ser Gln Asp Ile Gly Ile Ser Leu Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 47

Ala Thr Ser Ser Leu Asp Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 48

Leu Gln Tyr Ala Ser Ser Pro Tyr Thr
1               5
```

<210> SEQ ID NO 49
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 49

```
Gln Val Gln Leu Gln Gln Pro Gly Ala Asp Leu Val Arg Pro Gly Ala
1               5                   10                  15

Ser Val Thr Leu Ser Cys Lys Ala Ser Gly Tyr Ser Phe Thr Ser Tyr
            20                  25                  30

Trp Met Asn Trp Val Lys Gln Arg Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Arg Ser Pro Thr Ser Glu Asp Ser Ala Val Tyr Tyr Cys
                85                  90                  95

Ala Gly Leu Thr Ile Tyr Phe Asp Tyr Trp Gly Gln Gly Thr Thr Leu
            100                 105                 110

Thr Val Ser Ser
        115
```

<210> SEQ ID NO 50
<211> LENGTH: 348
<212> TYPE: DNA
<213> ORGANISM: Artificial Sequence
<220> FEATURE:
<223> OTHER INFORMATION: Synthetic Sequence

<400> SEQUENCE: 50

```
caggtccaac tacagcagcc tggggctgac ctggtgaggc ctggagcttc agtgacgctg    60
tcctgcaagg cttctggcta ctccttcacc agctactgga tgaactgggt gaagcagagg   120
cctggacaag gcctggagtg gattggcatg attcatcctt ccgatagtga aactaggtta   180
aatcagaagt tcaaggacaa ggccacattg actgtagaca aatcctccag cacagcctac   240
atgcaactcc gcagcccgac atctgaggac tctgcggtct attactgtgc aggcctaact   300
atttactttg actattgggg ccaaggcacc actctcacag tctcctca                348
```

<210> SEQ ID NO 51
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 51

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ile Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80
```

Glu Asp Phe Val Asp Tyr Tyr Cys Leu Gln Tyr Ala Ser Ser Pro Tyr
                85                  90                  95

Thr Phe Gly Gly Gly Thr Lys Leu Glu Ile Lys
            100                 105

<210> SEQ ID NO 52
<211> LENGTH: 321
<212> TYPE: DNA
<213> ORGANISM: Artificial Sequence
<220> FEATURE:
<223> OTHER INFORMATION: Synthetic Sequence

<400> SEQUENCE: 52
gacatccaga tgacccagtc tccatcctcc ttatctgcct ctctgggaga aagagtcagt      60
ctcacttgtc gggcaagtca ggacattggt attagcttaa actggcttca gcaggaacca     120
gatggaacta ttaaacgcct gatctacgcc acatccagtt tagattctgg tgtccccaaa     180
aggttcagtg gcagtaggtc tgggtcagat tattctctca ccatcagcag ccttgagtct     240
gaagattttg tagactatta ctgtctacaa tatgctagtt ctccgtacac gttcggaggg     300
gggaccaagc tggaaataaa a                                               321

<210> SEQ ID NO 53
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Met Ile His Pro Ser Asp Ser Glu Thr Arg Leu Asn Gln Lys Phe
    50                  55                  60

Met Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Leu Tyr Gly Asn Ser Trp Gly Gln Gly Thr Leu Val Thr
            100                 105                 110

Val Ser Ser
        115

<210> SEQ ID NO 54
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ile Ser
            20                  25                  30

```
Leu Asn Trp Tyr Gln Gln Lys Pro Gly Lys Ala Pro Lys Arg Leu Ile
             35                  40                  45

Tyr Ala Thr Ser Ser Leu Asp Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Ala Ser Ser Pro Tyr
                 85                  90                  95

Thr Phe Gly Gln Gly Thr Lys Val Glu Ile Lys
            100                 105
```

<210> SEQ ID NO 55
<211> LENGTH: 345
<212> TYPE: DNA
<213> ORGANISM: Artificial Sequence
<220> FEATURE:
<223> OTHER INFORMATION: Synthetic Sequence

<400> SEQUENCE: 55

```
caggtgcagc tggtccaatc cggggctgag gtgaagaagc ctggagcatc agtgaaagtt      60
tcatgcaaag ctagtggtta caccttcacc agctattgga tgaactgggt gcggcaggcc     120
cccggtcagg gcttgagtg gatgggcatg atccacccat ccgactctga gactaggctg      180
aaccagaagt ttatggatag agtgaccatg acaagagata cgtccacttc tactgtctat     240
atggaactga gcagtctgag atctgaagac acagccgttt actactgtgc tcgcggactc     300
tatggcaata gctggggcca aggaacattg gtaaccgtct cttct                     345
```

<210> SEQ ID NO 56
<211> LENGTH: 321
<212> TYPE: DNA
<213> ORGANISM: Artificial Sequence
<220> FEATURE:
<223> OTHER INFORMATION: Synthetic Sequence

<400> SEQUENCE: 56

```
gacatccaga tgacccaatc tccctcctcc ctgagcgcat ccgtggggga tagagtgacc      60
ataacctgcc gggcctctca ggacatcggt atttctttga attggtatca gcagaagccc     120
gggaaggccc ctaaacgcct gatctatgct acttccagtc tggacagcgg ggtcccgtca     180
aggttttcag gcagtggatc aggcacagag tttacactca aatttcgag cctgcagcct      240 gaagatttcg ccacttatta ctgtcttcaa tacgctagct ctccatacac gttcggccag     300
ggaaccaagg ttgagattaa a                                                321
```

<210> SEQ ID NO 57
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 57

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Trp Met Asn Trp Val Arg Gln Ala Pro Gly Gln Gly Leu Glu Trp Met
             35                  40                  45

Gly Met Ile His Pro Ser Asp Ser Glu Thr Arg Leu Asn Gln Lys Phe
```

```
                    50                  55                  60

Met Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                     85                  90                  95

Ala Arg Gly Leu Tyr Gly Asn Ser Trp Gly Gln Gly Thr Leu Val Thr
                100                 105                 110

Val Ser Ser
        115

<210> SEQ ID NO 58
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 58

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Gly Ile Ser
                 20                  25                  30

Leu Asn Trp Leu Gln Gln Glu Pro Gly Lys Ala Pro Lys Arg Leu Ile
             35                  40                  45

Tyr Ala Thr Ser Ser Leu Asp Ser Gly Val Pro Lys Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Ala Ser Ser Pro Tyr
                     85                  90                  95

Thr Phe Gly Gln Gly Thr Lys Val Glu Ile Lys
                100                 105

<210> SEQ ID NO 59
<211> LENGTH: 345
<212> TYPE: DNA
<213> ORGANISM: Artificial Sequence
<220> FEATURE:
<223> OTHER INFORMATION: Synthetic Sequence

<400> SEQUENCE: 59
caggtgcagc tggtccaatc cggggctgag gtgaagaagc ctggagcatc agtgaaagtt      60
tcatgcaaag ctagtggtta caccttcacc agctattgga tgaactgggt gcggcaggcc     120
cccggtcagg ggcttgagtg gatgggcatg atccacccat ccgactctga gactaggctg     180
aaccagaagt ttatggatag agtgaccatg acaagagata cgtccacttc tactgtctat     240
atggaactga gcagtctgag atctgaagac acagccgttt actactgtgc tcgcggactc     300
tatggcaata gctggggcca aggaacattg gtaaccgtct cttct                     345

<210> SEQ ID NO 60
<211> LENGTH: 321
<212> TYPE: DNA
<213> ORGANISM: Artificial Sequence
<220> FEATURE:
<223> OTHER INFORMATION: Synthetic Sequence

<400> SEQUENCE: 60
gacatccaga tgactcagtc cccctcgagc ctctcagctt ctgttggaga cagagtgaca      60
```

```
attacatgcc gggcctcaca ggatattggg atctccctga actggctgca acaggaacca    120
ggaaaggccc ctaagcgcct gatatatgcc acatcctctc ttgactcagg ggtcccaaag    180
aggtttagcg gcagtggatc aggtactgag ttcactctca ccatctctag cctgcagcct    240
gaggattttg caacctacta ttgtttgcaa tacgctagtt ccccctacac gttcggccag    300
ggcaccaaag tggaaatcaa a                                              321
```

```
<210> SEQ ID NO 61
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Arg Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Met Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Leu Tyr Gly Asn Ser Trp Gly Gln Gly Thr Leu Val Thr
            100                 105                 110

Val Ser Ser
        115
```

```
<210> SEQ ID NO 62
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ile Ser
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Ala Ser Ser Pro Tyr
                85                  90                  95

Thr Phe Gly Gln Gly Thr Lys Val Glu Ile Lys
            100                 105
```

```
<210> SEQ ID NO 63
<211> LENGTH: 345
<212> TYPE: DNA
```

-continued

<213> ORGANISM: Artificial Sequence
<220> FEATURE:
<223> OTHER INFORMATION: Synthetic Sequence

<400> SEQUENCE: 63

```
caagtccagc tcgtgcagtc tggcgctgag gtgaaaaagc ccggggcctc agtgaaggtt      60
tcttgcaagg caagcggcta cacctttacc tcctattgga tgaattgggt gcgacagcgg     120
ccaggccagg ggttggagtg gatcggaatg attcaccctc gtgactcaga aactaggctg     180
aaccagaaat tcatggacag agtcacaatg acgcgcgata caagcactag tacagtttac     240
atggagctga gcagcctgag atcggaagat actgccgtgt attactgtgc taggggactg     300
tatggaaact cttggggtca aggcacccct gtaaccgtct cctcc                     345
```

<210> SEQ ID NO 64
<211> LENGTH: 321
<212> TYPE: DNA
<213> ORGANISM: Artificial Sequence
<220> FEATURE:
<223> OTHER INFORMATION: Synthetic Sequence

<400> SEQUENCE: 64

```
gacatccaga tgacccaatc tccctcctcc ctgagcgcat ccgtggggga tagagtgacc      60
ataacctgcc gggcctctca ggacatcggt atttctttga attggtatca gcagaagccc     120
gggaaggccc ctaaacgcct gatctatgct acttccagtc tggacagcgg ggtcccgtca     180
aggttttcag gcagtggatc aggcacagag tttacactca caatttcgag cctgcagcct     240
gaagatttcg ccacttatta ctgtcttcaa tacgctagct ccatacac gttcggccag       300
ggaaccaagg ttgagattaa a                                                321
```

<210> SEQ ID NO 65
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 65

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Arg Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Met Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Leu Tyr Gly Asn Ser Trp Gly Gln Gly Thr Leu Val Thr
            100                 105                 110

Val Ser Ser
        115
```

<210> SEQ ID NO 66
<211> LENGTH: 107
<212> TYPE: PRT
<213> ORGANISM: Artificial Sequence

```
<220> FEATURE:
<223> OTHER INFORMATION: Synthetic Sequence

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ile Ser
            20                  25                  30

Leu Asn Trp Leu Gln Gln Glu Pro Gly Lys Ala Pro Lys Arg Leu Ile
        35                  40                  45

Tyr Ala Thr Ser Ser Leu Asp Ser Gly Val Pro Lys Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Ala Ser Ser Pro Tyr
                85                  90                  95

Thr Phe Gly Gln Gly Thr Lys Val Glu Ile Lys
            100                 105

<210> SEQ ID NO 67
<211> LENGTH: 345
<212> TYPE: DNA
<213> ORGANISM: Artificial Sequence
<220> FEATURE:
<223> OTHER INFORMATION: Synthetic Sequence

<400> SEQUENCE: 67
caagtccagc tcgtgcagtc tggcgctgag gtgaaaaagc ccggggcctc agtgaaggtt      60
tcttgcaagg caagcggcta cacctttacc tcctattgga tgaattgggt gcgacagcgg     120
ccaggccagg ggttggagtg gatcggaatg attcaccecta gtgactcaga aactaggctg     180
aaccagaaat tcatggacag agtcacaatg acgcgcgata caagcactag tacagtttac     240
atggagctga gcagcctgag atcggaagat actgccgtgt attactgtgc tagggactg      300 tatggaaact cttggggtca aggcacccett gtaaccgtct cctcc                    345

<210> SEQ ID NO 68
<211> LENGTH: 321
<212> TYPE: DNA
<213> ORGANISM: Artificial Sequence
<220> FEATURE:
<223> OTHER INFORMATION: Synthetic Sequence

<400> SEQUENCE: 68
gacatccaga tgactcagtc cccctcgagc ctctcagctt ctgttggaga cagagtgaca      60
attacatgcc gggcctcaca ggatattggg atctccctga actggctgca acaggaacca     120
ggaaaggccc ctaagcgcct gatatatgcc acatcctctc ttgactcagg ggtcccaaag     180
aggtttagcg gcagtggatc aggtactgag ttcactctca ccatctctag cctgcagcct     240
gaggattttg caacctacta ttgtttgcaa tacgctagtt cccctacac gttcggccag      300 ggcaccaaag tggaaatcaa a                                               321
```